(12) United States Patent
Hirszowicz et al.

(10) Patent No.: US 9,439,662 B2
(45) Date of Patent: *Sep. 13, 2016

(54) BALLOON CATHETER

(71) Applicant: ANGIOSLIDE LTD., Natania (IL)

(72) Inventors: Eran Hirszowicz, Ramat-Gan (IL); Shay Dubi, Tel-Aviv (IL)

(73) Assignee: AngioSlide Ltd., Natania (IL)

( * ) Notice: Subject to any disclaimer, the term of this patent is extended or adjusted under 35 U.S.C. 154(b) by 433 days.

This patent is subject to a terminal disclaimer.

(21) Appl. No.: 14/012,624

(22) Filed: Aug. 28, 2013

(65) Prior Publication Data

US 2015/0066068 A1 Mar. 5, 2015
US 2016/0051270 A9 Feb. 25, 2016

Related U.S. Application Data

(63) Continuation of application No. 11/477,812, filed on Jun. 30, 2006, now Pat. No. 8,556,851.

(60) Provisional application No. 60/695,868, filed on Jul. 5, 2005, provisional application No. 60/726,160, filed on Oct. 14, 2005.

(51) Int. Cl.
  *A61M 29/00* (2006.01)
  *A61B 17/22* (2006.01)

(52) U.S. Cl.
  CPC ............... *A61B 17/22032* (2013.01)

(58) Field of Classification Search
  CPC ........................................ A61B 17/22032
  USPC ........................................ 606/194
  See application file for complete search history.

(56) References Cited

U.S. PATENT DOCUMENTS 4,004,588 A 1/1977 Alexander
4,243,040 A * 1/1981 Beecher .................. 606/127
(Continued)

FOREIGN PATENT DOCUMENTS

CA 2183214 2/1998
CN 1322145 11/2001
(Continued)

OTHER PUBLICATIONS

Communication Pursuant to Article 94(3) and Rule 71(1) EPC Dated Jan. 28, 2010 From the European Patent Office Re. Application No. 07766874.7.
(Continued)

*Primary Examiner* — Katherine M Shi
*Assistant Examiner* — Mohamed Gabr

(57) ABSTRACT

A balloon catheter includes an outer conduit having an outer surface, and an inner conduit having an outer surface. The inner conduit is suitable for passage over a guide wire, and the inner conduit is movably disposed within the lumen of the outer conduit. There is also a balloon having a proximal margin and a distal margin, such that the proximal margin of the balloon is attached to the outer surface of the distal tip of the outer conduit and the distal margin of the balloon is attached to the outer surface of the portion of the inner conduit that extends beyond the distal tip of the outer conduit. And there is a fluid port for introducing an expansion fluid into the annular space formed between the inner surface of the outer conduit and the outer surface of the inner conduit and into the lumen of the balloon, and for the removal of the expansion fluid.

20 Claims, 7 Drawing Sheets

(56) References Cited

U.S. PATENT DOCUMENTS

| | | |
|---|---|---|
| 4,271,839 A | 6/1981 | Fogarty et al. |
| 4,469,100 A | 9/1984 | Harwick et al. |
| 4,597,389 A | 7/1986 | Ibrahim |
| 4,611,594 A | 9/1986 | Grayhack et al. |
| 4,748,982 A | 6/1988 | Horzewski et al. |
| 4,762,129 A | 8/1988 | Bonzel |
| 4,820,270 A | 4/1989 | Hardcastle et al. |
| 4,846,174 A | 7/1989 | Willard et al. |
| 4,946,440 A | 8/1990 | Hall |
| 4,955,895 A | 9/1990 | Sugiyama et al. |
| 4,968,300 A | 11/1990 | Moutafis et al. |
| 5,019,041 A | 5/1991 | Robinson et al. |
| 5,074,845 A | 12/1991 | Miraki et al. |
| 5,092,839 A | 3/1992 | Kipperman |
| 5,109,830 A | 5/1992 | Cho |
| 5,254,091 A | 10/1993 | Aliahmad et al. |
| 5,307,814 A | 5/1994 | Kressel et al. |
| RE34,633 E | 6/1994 | Sos et al. |
| 5,338,298 A | 8/1994 | McIntyre |
| 5,421,826 A | 6/1995 | Crocker et al. |
| 5,437,638 A | 8/1995 | Bowman |
| 5,445,646 A | 8/1995 | Euteneuer et al. |
| 5,470,314 A | 11/1995 | Walinsky |
| 5,534,007 A | 7/1996 | St. Germain et al. |
| 5,630,822 A | 5/1997 | Hermann et al. |
| 5,785,675 A | 7/1998 | Drasler et al. |
| 5,865,801 A | 2/1999 | Houser |
| 5,868,767 A | 2/1999 | Farley et al. |
| 5,941,895 A | 8/1999 | Myler et al. |
| 5,968,012 A | 10/1999 | Ren et al. |
| 6,004,341 A | 12/1999 | Zhu et al. |
| 6,022,359 A | 2/2000 | Frantzen |
| 6,039,721 A | 3/2000 | Johnson et al. |
| 6,063,057 A | 5/2000 | Choh |
| 6,129,706 A | 10/2000 | Janacek |
| 6,152,947 A | 11/2000 | Ambrisco et al. |
| 6,159,230 A | 12/2000 | Samuels |
| 6,179,827 B1 | 1/2001 | Davis et al. |
| 6,280,412 B1 | 8/2001 | Pederson, Jr. et al. |
| 6,383,195 B1 | 5/2002 | Richard |
| 6,695,810 B2 | 2/2004 | Peacock, III et al. |
| 7,172,576 B2 | 2/2007 | Sawa et al. |
| 7,201,770 B2 | 4/2007 | Johnson et al. |
| 7,563,270 B2 | 7/2009 | Gumm |
| 7,591,831 B2 | 9/2009 | Parsonage et al. |
| 7,824,345 B2 | 11/2010 | Euteneuer et al. |
| 2002/0082639 A1 | 6/2002 | Broome et al. |
| 2002/0091398 A1 | 7/2002 | Galdonik et al. |
| 2002/0121472 A1 | 9/2002 | Garner et al. |
| 2002/0177870 A1 | 11/2002 | Sepetka et al. |
| 2003/0028211 A1 | 2/2003 | Crocker et al. |
| 2003/0055483 A1 | 3/2003 | Gumm |
| 2003/0093107 A1 | 5/2003 | Parsonage et al. |
| 2003/0105508 A1 | 6/2003 | Johnson et al. |
| 2003/0130672 A1 | 7/2003 | DoBrava et al. |
| 2003/0176884 A1 | 9/2003 | Berrada et al. |
| 2003/0176910 A1 | 9/2003 | Vrba et al. |
| 2003/0208223 A1 | 11/2003 | Kleiner |
| 2004/0049223 A1 | 3/2004 | Nishtala et al. |
| 2004/0054362 A1 | 3/2004 | Lopath et al. |
| 2004/0073243 A1 | 4/2004 | Sepetka et al. |
| 2004/0236275 A1 | 11/2004 | Pruitt et al. |
| 2004/0236367 A1 | 11/2004 | Brown et al. |
| 2005/0004553 A1 | 1/2005 | Douk |
| 2005/0085826 A1 | 4/2005 | Nair et al. |
| 2005/0101986 A1 | 5/2005 | Daniel et al. |
| 2005/0102019 A1 | 5/2005 | Yadin |
| 2005/0137501 A1 | 6/2005 | Euteneuer et al. |
| 2005/0137607 A1 | 6/2005 | Assell et al. |
| 2005/0154414 A1 | 7/2005 | Perreault |
| 2005/0187570 A1 | 8/2005 | Nguyen et al. |
| 2005/0209629 A1 | 9/2005 | Kerr et al. |
| 2005/0261705 A1 | 11/2005 | Gist |
| 2005/0288700 A1 | 12/2005 | Chermoni |
| 2006/0015134 A1 | 1/2006 | Trinidad |
| 2006/0025720 A1 | 2/2006 | Sawa et al. |
| 2006/0129107 A1 | 6/2006 | McArthur et al. |
| 2006/0129710 A1 | 6/2006 | O'Connor et al. |
| 2007/0083158 A1 | 4/2007 | Hirszowicz et al. |
| 2007/0088380 A1 | 4/2007 | Hirszowicz et al. |
| 2007/0255305 A1 | 11/2007 | McMichael et al. |
| 2009/0112239 A1 | 4/2009 | To |
| 2009/0171278 A1 | 7/2009 | Hirszowicz et al. |
| 2009/0204069 A1 | 8/2009 | Hirszowicz et al. |
| 2009/0247945 A1 | 10/2009 | Levit et al. |
| 2009/0270902 A1 | 10/2009 | Assell et al. |
| 2010/0010303 A1 | 1/2010 | Bakos |
| 2010/0016792 A1 | 1/2010 | Hirszowicz |
| 2010/0022970 A1 | 1/2010 | Hirszowicz |
| 2011/0275990 A1 | 11/2011 | Besser et al. |
| 2012/0302996 A1 | 11/2012 | Barash et al. |
| 2013/0006291 A1 | 1/2013 | Harari et al. |
| 2013/0060234 A1 | 3/2013 | Besser et al. |
| 2015/0126966 A1 | 5/2015 | Hirszowicz et al. |
| 2015/0306361 A1 | 10/2015 | Feig et al. |

FOREIGN PATENT DOCUMENTS

| | | |
|---|---|---|
| EP | 0200668 | 12/1986 |
| EP | 0 359 489 | 9/1989 |
| EP | 0 380 873 | 12/1989 |
| EP | 0366478 | 5/1990 |
| EP | 0399712 | 11/1990 |
| EP | 0987045 | 3/2000 |
| EP | 1120129 | 8/2001 |
| EP | 1124504 | 8/2001 |
| EP | 1333778 | 5/2002 |
| EP | 1333778 | 8/2003 |
| EP | 1753348 | 2/2007 |
| EP | 1 062 966 | 6/2011 |
| GB | 0 254 385 | 2/1981 |
| IL | 178738 | 2/2007 |
| JP | 54-066582 | 5/1979 |
| JP | 59-502134 | 12/1984 |
| JP | 61-293474 | 12/1986 |
| JP | 02-119875 | 5/1990 |
| JP | 2000-005189 | 1/2000 |
| JP | 2000005189 A | 1/2000 |
| JP | 2002-520099 | 7/2002 |
| JP | 2003-126263 | 5/2003 |
| JP | 2004-329485 | 11/2004 |
| WO | 84/01513 | 4/1984 |
| WO | WO 95/17223 | 6/1995 |
| WO | 98/29026 | 7/1998 |
| WO | WO 00/02613 | 1/2000 |
| WO | WO 00/27309 | 5/2000 |
| WO | 00/38776 | 7/2000 |
| WO | 0238084 | 5/2002 |
| WO | WO 02/38084 | 5/2002 |
| WO | 02/055146 | 7/2002 |
| WO | 2004/014240 | 2/2004 |
| WO | WO 2004/014240 | 2/2004 |
| WO | WO 2004/017865 | 3/2004 |
| WO | WO 2004/028611 | 4/2004 |
| WO | 2004/082462 | 9/2004 |
| WO | WO 2004/098681 | 11/2004 |
| WO | 2005/000130 | 1/2005 |
| WO | WO 2005/030308 | 4/2005 |
| WO | 2005/041788 | 5/2005 |
| WO | WO 2005/102184 | 11/2005 |
| WO | WO 2005/112783 | 12/2005 |
| WO | WO 2007/004221 | 1/2007 |
| WO | WO 2007/042935 | 4/2007 |
| WO | WO 2007/042936 | 4/2007 |
| WO | WO 2007/132464 | 11/2007 |
| WO | WO 2008/004238 | 1/2008 |
| WO | WO 2008/004239 | 1/2008 |
| WO | WO 2009/053839 | 4/2009 |
| WO | WO 2010/001404 | 1/2010 |
| WO | WO 2010/001405 | 1/2010 |
| WO | WO 2010/079494 | 7/2010 |
| WO | WO 2011/036667 | 3/2011 |
| WO | WO 2011/080731 | 7/2011 |

(56) References Cited

FOREIGN PATENT DOCUMENTS

| | | |
|---|---|---|
| WO | WO 2011/080732 | 7/2011 |
| WO | WO 2011/089599 | 7/2011 |
| WO | WO 2014/087395 | 6/2014 |

OTHER PUBLICATIONS

Communication Pursuant to Article 94(3) EPC Dated Apr. 4, 2012 From the European Patent Office Re. Application No. 10170623.2.
Communication Pursuant to Article 94(3) EPC Dated Mar. 10, 2011 From the European Patent Office Re. Application No. 07766875.4.
Communication Pursuant to Article 94(3) EPC Dated Feb. 23, 2010 From the European Patent Office Re. Application No. 07766875.4.
Communication Pursuant to Article 94(3) EPC Dated Jan. 28, 2010 From the European Patent Office Re. Application No. 07766874.7.
Communication Pursuant to Article 94(3) EPC Dated Dec. 29, 2008 From the European Patent Office Re. Application No. 05735055.5.
Communication Pursuant to Article 94(3) EPC Dated May 29, 2008 From the European Patent Office Re. Application No. 06766111.6.
Communication Pursuant to Article 94(3) EPC Dated Aug. 30, 2011 From the European Patent Office Re. Application No. 10170623.2.
Communication Pursuant to Article 96(2) EPC Dated Nov. 5, 2007 From the European Patent Office Re. Application No. 05735055.5.
Communication Pursuant to Rules 161(2) and 162 EPC Dated May 3, 2012 From the European Patent Office Re. Application No. 10818501.8.
Communication Pursuant to Rules 161(2) and 162 EPC Dated Feb. 14, 2011 From the European Patent Office Re. Application No. 09773059.2.
Communication Pursuant to Rules 161(2) and 162 EPC Dated Feb. 14, 2011 From the European Patent Office Re. Application No. 09773060.0.
Communication Pursuant to Rules 161(2) and 162 EPC Dated Jul. 15, 2015 From the European Patent Office Re. Application No. 13861353.4.
Decision of Patent Dated Mar. 6, 2012 From the Japanese Patent Office Re. Application No. 2007-509059 and Its Translation Into English.
Decision to Grant a European Patent Pursuant to Article 97(1) EPC Dated Aug. 12, 2010 From the European Patent Office Re. Application No. 10170623.2.
Decision to Grant a European Patent Pursuant to Article 97(1) EPC Dated Aug. 17, 2012 From the European Patent Office Re. Application No. 10169255.6.
Decision to Grant a European Patent Pursuant to Article 97(1) EPC Dated Jul. 19, 2010 From the European Patent Office Re. Application No. 05735055.5.
European Search Report and the European Search Opinion Dated Nov. 15, 2010 From the European Patent Office Re. Application No. 10169255.6.
European Search Report and the European Search Opinion Dated Nov. 26, 2010 From the European Patent Office Re. Application No. 10170623.2.
Examiner's Report Dated Feb. 2, 2011 From the Australian Government, IP Australia Re. Application No. 2006264397.
Final Rejection Dated Aug. 30, 2011 From the Japanese Patent Office Re. Application No. 2007-509059 and Its Translation Into English.
International Preliminary Report on Patentability Dated Jul. 4, 2012 From the International Bureau of WIPO Re. Application No. PCT/IL2010/000002.
International Preliminary Report on Patentability Dated Jan. 5, 2011 From the International Bureau of WIPO Re. Application No. PCT/IL2009/000667.
International Preliminary Report on Patentability Dated Jan. 5, 2011 From the International Bureau of WIPO Re. Application No. PCT/IL2009/000668.
International Preliminary Report on Patentability Dated Apr. 7, 2007 From the International Bureau of WIPO Re. Application No. PCT/IL2007/000845.
International Preliminary Report on Patentability Dated Apr. 7, 2009 From the International Bureau of WIPO Re. Application No. PCT/IL2007/000844.
International Preliminary Report on Patentability Dated Jan. 9, 2008 From the International Bureau of WIPO Re. Application No. PCT/IL2006/000770.
International Preliminary Report on Patentability Dated Jun. 9, 2015 From the International Bureau of WIPO Re. Application No. PCT/IL2013/000089.
International Preliminary Report on Patentability Dated Mar. 10, 2009 From the International Bureau of WIPO Re. Application No. PCT/IB2006/002955.
International Preliminary Report on Patentability Dated Jul. 12, 2011 From the International Bureau of WIPO Re. Application No. PCT/IL2009/000667.
International Preliminary Report on Patentability Dated Jul. 24, 2012 From the International Bureau of WIPO Re. Application No. PCT/1L2011/000060.
International Preliminary Report on Patentability Dated Oct. 25, 2006 From the International Bureau of WIPO Re. Application No. PCT/IL2005/000420.
International Preliminary Report on Patentability Dated Mar. 27, 2012 From the International Bureau of WIPO Re. Application No. PCT/IL2010/000797.
International Search Report and the Written Opinion Dated Jun. 1, 2010 From the International Searching Authority Re. Application No. PCT/IL2010/000025.
International Search Report and the Written Opinion Dated Nov. 3, 2006 From the International Searching Authority Re. Application No. PCT/IL2006/000770.
International Search Report and the Written Opinion Dated May 7, 2010 From the International Searching Authority Re. Application No. PCT/IL2010/000001.
International Search Report and the Written Opinion Dated Aug. 11, 2008 From the International Searching Authority Re. Application No. PCT/IL2007/000844.
International Search Report and the Written Opinion Dated Aug. 11, 2008 From the International Searching Authority Re. Application No. PCT/IL2007/000845.
International Search Report and the Written Opinion Dated May 12, 2010 From the International Searching Authority Re. Application No. PCT/IL2010/000002.
International Search Report and the Written Opinion Dated Feb. 23, 2011 From the International Searching Authority Re. Application No. PCT/IL2010/000797.
International Search Report and the Written Opinion Dated May 23, 2011 From the International Searching Authority Re. Application No. PCT/IL2011/000060.
International Search Report and the Written Opinion Dated Mar. 26, 2014 From the International Searching Authority Re. Application No. PCT/IL2013/000089.
International Search Report and the Written Opinion Dated Oct. 28, 2009 From the International Searching Authority Re. Application No. PCT/IL2009/000667.
International Search Report and the Written Opinion Dated Oct. 28, 2009 From the International Searching Authority Re. Application No. PCT/IL2009/000668.
International Search Report and the Written Opinion Dated Jul. 29, 2005 From the International Searching Authority Re. Application No. PCT/IL2005/000420.
International Search Report and the Written Opinion Dated Oct. 29, 2008 From the International Searching Authority Re. Application No. PCT/IB2006/002955.
Invitation Pursuant to Article 94(3) and Rule 71(1) EPC Dated Dec. 19, 2013 From the European Patent Office Re. Application No. 10170623.2.
Notice of Refusal Dated May 19, 2014 From the Israel Patent Office Re. Application No. 211022.
Notice of the Reason for Rejection Dated May 13, 2013 From the Korean Intellectual Property Office Re. Application No. 10-2008-7010935.
Notification of Grounds for Rejection Dated Aug. 16, 2011 From the Japanese Patent Office Re. Application No. 2008-519139 and Its Translation Into English.
Notification of Grounds for Rejection Dated Oct. 25, 2011 From the Japanese Patent Office Re. Application No. 2008-535127 and Its Translation Into English.

(56) References Cited

OTHER PUBLICATIONS

Notification of Office Action Dated Oct. 24, 2012 From the State Intellectual Property Office of the People's Republic of China Re. Application No. 200980132738.0.
Notification of the Decision to Grant a Patent Right for Patent for Invention Dated Mar. 6, 2013 From the Patent Office of the People's Republic of China Re. Application No. 201010224944.9 and Its Translation Into English.
Notification of the Decision to Grant a Patent Right for Patent for Invention Dated Apr. 20, 2010 From the Patent Office of the People's Republic of China Re. Application No. 200580020733.0 and Its Translation Into English.
Office Action and Search Report Dated Apr. 2, 2013 From the State Intellectual Property Office of the People's Republic of China Re. Application No. 201210018835.0 and Its Translation Into English.
Office Action and Search Report Dated Aug. 4, 2014 From the State Intellectual Property Office of the People's Republic of China Re. Application No. 201310193577.4 and Its Translation Into English.
Office Action and Search Report Dated Aug. 31, 2012 From the State Intellectual Property Office of the People's Republic of China Re. Application No. 201010224944.9 and Its Translation Into English.
Office Action Dated Sep. 2, 2014 From the State Intellectual Property Office of the People's Republic of China Re. Application No. 201210018835.0 and Its Translation Into English.
Office Action Dated Mar. 5, 2012 From the Israel Patent Office Re. Application No. 178738.
Office Action Dated Mar. 5, 2012 From the Israel Patent Office Re. Application No. 211022.
Office Action Dated Jun. 6, 2012 From the Israel Patent Office Re. Application No. 211023.
Office Action Dated Mar. 6, 2012 From the State Intellectual Property Office of the People's Republic of China Re. Application No. 200680032507.9 and Its Translation Into English.
Office Action Dated Oct. 8, 2012 From the State Intellectual Property Office of the People's Republic of China Re. Application No. 200680047235.X and Its Translation Into English.
Office Action Dated Nov. 9, 2009 From the Israel Patent Office Re. Application No. 178738.
Office Action Dated Aug. 12, 2011 From the State Intellectual Property Office of the People's Republic of China Re. Application No. 200680032507.9 and Its Translation Into English.
Office Action Dated Jan. 12, 2012 From the State Intellectual Property Office of the People's Republic of China Re. Application No. 201010224944.9 and Its Translation into English.
Office Action Dated Jun. 12, 2009 From the State intellectual Property Office of the People's Republic of China Re. Application No. 200580020733.0 and Its Translation Into English.
Office Action Dated Apr. 13, 2015 From the State Intellectual Property Office of the People's Republic of China Re. Application No. 201310193577.4 and Its Translation Into English.
Office Action Dated Mar. 17, 2011 From the Israel Patent Office Re. Application No. 178738.
Office Action Dated Jun. 23, 2011 From the State Intellectual Property Office of the People's Republic of China Re. Application No. 201010224944.9 and Its Translation Into English.
Office Action Dated Oct. 23, 2009 From the State Intellectual Property Office of the People's Republic of China Re. Application No. 200680032507.9 and Its Translation Into English.
Office Action Dated Dec. 24, 2013 From the State Intellectual Property Office of the People's Republic of China Re. Application No. 201210018835.0 and Its Translation Into English.
Office Action Dated Oct. 25, 2011 From the State Intellectual Property Office of the People's Republic of China Re. Application No. 200680047235.X and Its Translation Into English.
Official Action Dated Dec. 5, 2011 From the US Patent and Trademark Office Re. U.S. Appl. No. 12/901,535.
Official Action Dated Dec. 8, 2009 From the US Patent and Trademark Office Re. U.S. Appl. No. 11/587,179.
Official Action Dated May 12, 2015 From the US Patent and Trademark Office Re. U.S. Appl. No. 13/522,717.
Official Action Dated Aug. 18, 2010 From the US Patent and Trademark Office Re. U.S. Appl. No. 12/083,436.
Official Action Dated Jul. 19, 2012 From the US Patent and Trademark Office Re. U.S. Appl. No. 12/083,436.
Official Action Dated Apr. 20, 2015 From the US Patent and Trademark Office Re. U.S. Appl. No. 13/497,055.
Official Action Dated May 20, 2011 From the US Patent and Trademark Office Re. U.S. Appl. No. 12/083,436.
Official Action Dated Dec. 21, 2012 From the US Patent and Trademark Office Re. U.S. Appl. No. 13/001,433.
Official Action Dated Sep. 26, 2014 From the US Patent and Trademark Office Re. U.S. Appl. No. 13/497,055.
Requisition by the Examiner Dated Feb. 7, 2015 From the Canadian Intellectual Property Office Re. Application No. 2,563,657.
Requisition by the Examiner Dated Mar. 19, 2013 From the Canadian Intellectual Property Office Re. Application No. 2,613,713.
Restriction Official Action Dated May 13, 2009 From the US Patent and Trademark Office Re. U.S. Appl. No. 11/587,179.
Restriction Official Action Dated Mar. 17, 2013 From the US Patent and Trademark Office Re. U.S. Appl. No. 13/522,717.
Restriction Official Action Dated Jan. 20, 2011 From the US Patent and Trademark Office Re. U.S. Appl. No. 12/306,934.
Restriction Official Action Dated Jan. 21, 2011 From the US Patent and Trademark Office Re. U.S. Appl. No. 12/306,933.
Restriction Official Action Dated Oct. 25, 2012 From the US Patent and Trademark Office Re. U.S. Appl. No. 13/001,433.
Statement of Opinion Dated Sep. 10, 2013 From the Korean Intellectual Property Office Re. Application No. 10-2008-7001219 and Its Translation Into English.
Supplementary European Search Report and the European Search Opinion Dated Nov. 8, 2013 From the European Patent Office Re. Application No. 06809092.7.
Supplementary European Search Report and the European Search Opinion Dated Sep. 16, 2011 From the European Patent Office Re. Application No. 09773059.2.
Supplementary Partial European Search Report and the European Search Opinion Dated Nov. 19, 2009 From the European Patent Office Re. Application No. 07766875.4.
Translation of Notice of Reasons for Rejection Dated Dec. 14, 2010 From the Japanese Patent Office Re. Application No. 2007-509059.
Translation of Office Action Dated Sep. 19, 2010 From the State Intellectual Property Office of the People's Republic of China Re. Application No. 200680032507.9.
Translation of Office Action Dated Jan. 21, 2013 From the State Intellectual Property Office of the People's Republic of China Re. Application No. 200680032507.9.
Translation of Rejection Decision Dated Aug. 31, 2012 From the State Intellectual Property Office of the People's Republic of China Re. Application No. 200680032507.9.
Official Action Dated Oct. 16, 2015 From the US Patent and Trademark Office Re. U.S. Appl. No. 13/522,717.
Supplementary European Search Report and the European Search Opinion Dated Jul. 18, 2011 From the European Patent Office Re. Application No. 09773060.0.
Supplementary Partial European Search Report and the European Search Opinion Dated Oct. 19, 2009 From the European Patent Office Re. Application No. 07766874.7.
Examination Report Dated Dec. 31, 2012 From the Government of India, Patent Office, Intellectual Property Building Re. Application No. 3402/KOLNP/2006.
Examination Report Under Sections 12 & 13 of the Patents Act, 1970 and the Patents Rules, 2003 Dated May 10, 2016 From the Government of India, Patent Office, Intellectual Property Building Re. Application No. 439/KOLNP/2008.
Supplementary European Search Report Dated Jul. 1, 2016 From the European Patent Office Re. Application No. 13861353.4.

* cited by examiner

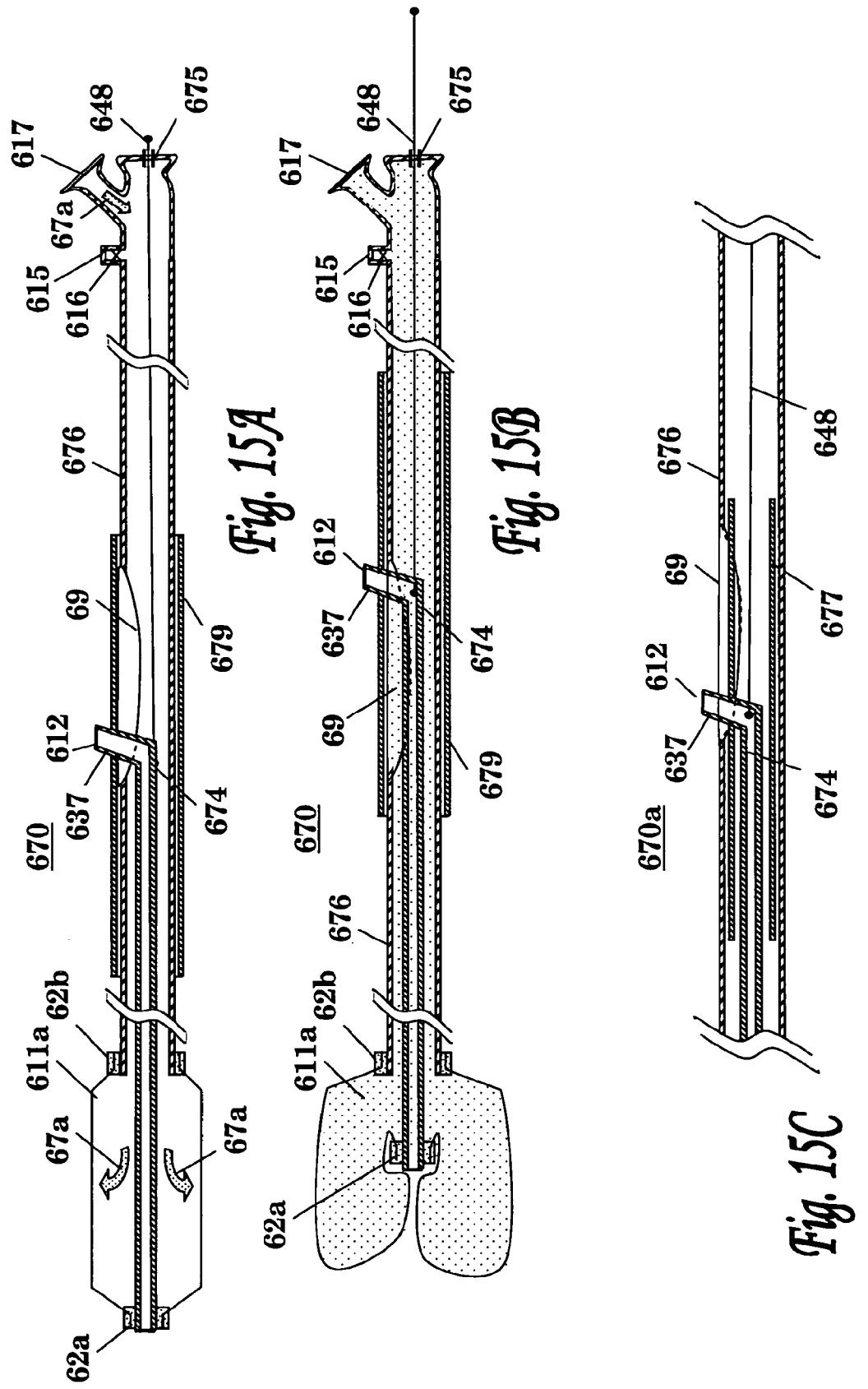

BALLOON CATHETER

RELATED APPLICATIONS

This application is a continuation of U.S. patent application Ser. No. 11/477,812 filed Jun. 30, 2006, now U.S. Pat. No. 8,556,851, which claims the benefit of priority of U.S. Provisional Patent Application No. 60/695,868 filed Jul. 5, 2005 and 60/726,160 filed Oct. 14, 2005, the entire contents of each of which are hereby incorporated by reference.

FIELD OF THE INVENTION

The present invention relates to a catheter system suitable for the retrieval of debris and other solid or liquid matter from body passages, and the removal of said matter from the body. More particularly, the invention relates to catheter systems comprising two or more concentrically-arranged conduits and an inflatable element connected therebetween, wherein said inflatable element is arranged such that it may entrap solid or liquid matter in an internal annular cavity.

BACKGROUND OF THE INVENTION

Catheters are used in various interventional procedures for delivering therapeutic means to a treated site (e.g., body organ or passageway such as blood vessels). In many cases, a catheter with a small distal inflatable balloon is guided to the treated site. Once the balloon is in place it is inflated by the operator for affixing it in place, for expanding a blocked vessel, for placing treatment means (e.g., stent) and/or for delivering surgical tools (e.g. knives, drills etc.) to a desired site. In addition, catheter systems have also been designed and used for retrieval of objects such as stents from body passageways.

Two basic types of catheter have been developed for intravascular use: other-the-wire (OTW) catheters and rapid-exchange catheters.

OTW catheter systems are characterized by the presence of a full-length guide wire, such that when the catheter is in its in situ working position, said guide wire passes through the entire length of a lumen formed in, or externally attached to, the catheter. OTW systems have several operational advantages which are related to the use of a full length guide wire, including good stiffness and pushability, features which are important when maneuvering balloon catheters along tortuous and/or partially occluded blood vessels.

U.S. Pat. No. 6,039,721 describes a balloon catheter system comprising two concentrically-arranged conduits, with a balloon connected between the distal regions thereof. The catheter system permits both expansion/deflation of the balloon and alteration in the length of the balloon when in situ, such that the balloon may be moved between extended and intussuscepted conformations. The catheter system is constructed in order that it may be use for two main purposes: firstly, treatment (i.e. expansion) of different-length stenosed portions of blood vessels with a single balloon and secondly, the delivery of either stents or medication to intravascular lesions, wherein the stent or medication is contained within the distally-intussuscepted portion of the balloon. When used for multiple, differing-length lesion expansion, the balloon is inserted into blood vessel in a collapsed, shortened, intussuscepted conformation, and is advanced until it comes to rest in the region of the shortest lesion to be treated. The balloon is then inflated and the lesion treated (i.e. expanded). Following deflation of the balloon, the distal end of the catheter system is moved such that the balloon becomes positioned in the region of the next-shortest lesion to be treated. The effective length of the balloon is then increased by moving the inner conduit in relation to the proximal conduit, following which the balloon is again inflated and the lesion treated. In this way, a series of different length stenoses—in order from the shortest to the longest—may be treated using a single balloon. When used for stent delivery, the stent is pre-loaded into a proximal annular space formed as a result of balloon intussusception. The balloon is then moved to the desired site and the stent delivered by means of moving the inner conduit distally (in relation to the outer tube), thereby "unpeeling" the stent from the catheter.

WO 00/38776 discloses a dual-conduit balloon catheter system similar in basic design to that described above in relation to U.S. Pat. No. 6,039,721. This catheter system is intended for use in a vibratory mode in order to break through total occlusions of the vascular lumen. In order to fulfill this aim, the outer conduit has a variable stiffness along its length, while the inner conduit. In addition, the inner conduit while being intrinsically relatively flexible is stiffened by the presence of axial tensioning wires. These conduit design features are used in order to permit optimal translation of vibratory movements of the proximal end of the inner conduit into corresponding vibration of the distal tip thereof.

Rapid exchange ("monorail") catheters typically comprise a relatively short guide wire lumen provided in a distal section thereof, and a proximal guide wire exit port located between the catheter's distal and proximal ends. This arrangement allows exchange of the catheter over a relatively short guide wire, in a manner which is simple to perform and which can be carried out by a single operator. Rapid exchange catheters have been extensively described in the art, for example, U.S. Pat. Nos. 4,762,129, 4,748,982 and EP0380873.

Rapid exchange catheters are commonly used in Percutaneous Transluminal Coronary Angioplasty (PTCA) procedures, in which obstructed blood vessels are typically dilated by a distal balloon mounted on the catheter's distal end. A stent is often placed at the vessel's dilation zone to prevent reoccurrences of obstruction therein. The dilation balloon is typically inflated via an inflation lumen which extends longitudinally inside the catheter's shaft between the dilation balloon and the catheter's proximal end.

The guide wire lumen passes within a smaller section of the catheter's shaft length and it is accessed via a lateral port situated on the catheter's shaft. This arrangement, wherein the guidewire tube is affixed to the catheter's shaft at the location of its lateral port, usually prevents designers from developing new rapid exchange catheter implementations which requires manipulating its inner shaft. For example, extending or shortening the catheter's length during procedures may be advantageously exploited by physicians to distally extend the length of the catheter into a new site after or during its placement in the patient's artery, for example in order to assist with the passage of tortuous vessels or small diameter stenoses, or to allow in-situ manipulation of an inflated balloon at the distal end of the catheter.

The rapid exchange catheters of the prior art are therefore usually designed for carrying out a particular procedure and their implementations are relatively restricted as a consequence of the need for at least one catheter shaft to exit the catheter system laterally, between the proximal and distal ends of said system. Consequently, a need exists for a rapid exchange catheter that overcomes the above mentioned problems and which allows expanding the range of applications of such catheters.

Despite the large number of different balloon catheter systems currently available, a need still exists for a system that can efficiently and safely collect plaque debris and other particulate matter from the lumen of internal body passages such as pathologically-involved blood vessels.

The primary object of the present invention is, therefore, to provide a balloon catheter system capable of collecting samples and/or debris from the body treated site and reducing the risk of distal embolization of any material that may be dislodged during inflation of the balloon at the treated site.

Another aim is to provide such a system in which the balloon length may be substantially shortened during use without unduly increasing internal pressure.

A further aim is to provide such a system in which the catheter tubing is of a construction suitable for withstanding the forces generated during balloon folding and unfolding.

Yet another aim is to provide such a system in which the balloon is of a shape and constructions that permits both optimal debris entrapment and low-profile folding within the passages to be treated.

A further object of the present invention is to provide balloon catheter systems having the advantages outlined hereinabove, wherein said catheter systems are OTW systems.

A further object of the present invention to provide a rapid exchange catheter having an adjustable balloon length and shape which may be modified during a procedure.

Yet another object of the present invention to provide a rapid exchange balloon catheter wherein the shape and/or volume of a standard inflated balloon may be adjusted during a procedure. A still further object of the present invention to provide a rapid exchange balloon catheter capable of collecting samples and/or debris from the body treated site and reducing the risk of distal embolization of any material that may be dislodged during inflation of the balloon at the treated site.

Other objects and advantages of the invention will become apparent as the description proceeds.

SUMMARY OF THE INVENTION

The present invention is therefore primarily directed to a balloon catheter system comprising at least one inner conduit and one outer conduit mutually disposed one inside the other, such that their longitudinal axes either coincide or are substantially parallel to each other, said inner tube being movably disposed along a longitudinal (i.e. distal-proximal) axis wherein an inflatable element such as a balloon is attached between the distal regions of said conduits, the distal end of the balloon being attached to the distal region of the inner conduit, and the proximal end of the balloon being attached to the distal region of said outer conduit. The catheter system is constructed such that the longitudinal position of the inner conduit in relation to the outer conduit may be altered by means of moving the proximal end of the inner conduit (i.e. the end closest to the operator). In this way, the distal-proximal length of the outer surface of the balloon may be altered, such that the balloon may be caused to progressively move between an elongated, extended conformation and a shortened, terminally-intussuscepted conformation, wherein in the latter conformation, an open-ended inner cavity is created in the terminally-intussuscepted region of the balloon. In use, this inner cavity may be employed to entrap particulate debris, liquids and other objects and substances and safely remove same from the body passage in which the balloon catheter system is inserted. The inflatable element used in the presently-disclosed and described catheter system is of a shape that permits said element to meet the dual requirements of effective debris collection and low-profile delivery and retrieval. Thus, in one preferred embodiment the inflatable element is provided in the form of a balloon having, in its inflated state, a tapered shape with a rounded distal extremity. A further feature of the presently-disclosed system is the presence of means for preventing internal pressure changes that occur as a consequence of changing the length and conformation of the balloon.

Thus, in one aspect, the present invention provides an OTW balloon catheter system comprising an outer conduit; an inner conduit disposed within the lumen of said outer conduit such that the longitudinal axes of said inner and outer conduits are substantially parallel, and positioned such that the distal tip of said inner conduit extends beyond the distal tip of said outer conduit, wherein said inner conduit is capable of being moved along its longitudinal axis in relation to said outer conduit, and wherein the lumen of said inner conduit is suitable for allowing the passage of a guidewire therethrough; an angioplastic balloon whose proximal margin is attached to the outer surface of the distal tip of said outer conduit, and whose distal margin is attached to the outer surface of the portion of the inner conduit that extends beyond the distal tip of said outer conduit, and wherein the distal portion of said balloon is capable of intussusception upon proximal movement of said inner conduit in relation to said outer conduit; means for the introduction of an expansion fluid into the annular space formed between the inner surface of the outer conduit and the outer surface of the inner conduit and therefrom into the lumen of said balloon, and for the removal thereof, and means for preventing pressure changes within said annular space upon axial movement of said inner conduit in relation to said outer conduit.

In one preferred embodiment of the OTW balloon catheter system of the present invention, the inner and outer conduits are characterized by their ability to withstand axially directed forces in the range of between 2 and 20 Newton without undergoing significant deformation. In the context of the present invention, the term "significant deformation" refers to changes in conduit length in excess of 5% of the total length of said conduit. While these conduits may be constructed of any suitable material capable of withstanding the aforementioned forces, in a preferred embodiment, the inner and outer conduits are constructed either from a biocompatible polymer (which in a preferred embodiment is selected from the group consisting of braided nylon thread and nylon thread that has undergone orientation treatment) or from flexible stainless steel tube.

In one preferred embodiment of the present invention, the balloon is characterized by having, in its inflated state, a pre-folding profile, i.e. it has shape which is capable of assisting and guiding the intussusception of the distal portion thereof upon proximal movement of the inner conduit in relation to the outer conduit.

In one particularly preferred embodiment of the catheter system, the aforementioned balloon pre-folding profile is achieved by manufacturing the balloon such that it has (in its inflated state) a tapered shape with a rounded distal extremity.

Preferably, the balloon is constructed from Nylon 12, Pevax or mixtures thereof. It is to be recognized, however, that the balloon may also be constructed of any other suitable materials as are well known in the art, without deviating from the scope of the present invention as defined in the claims.

In one preferred embodiment, the aforementioned means for preventing pressure changes comprises a syringe-like structure positioned at the proximal end of the catheter system, wherein the barrel of said syringe-like structure is formed by an expanded portion of the outer conduit, and wherein the plunger of said structure co-axially surrounds the proximal end of the inner conduit, and is affixed thereto.

In another aspect, the present invention also provides a method for collecting debris from an internal passage of a mammalian subject comprising the steps of:

a) inserting an OTW balloon catheter system as defined hereinabove over a guidewire into said internal passage, and advancing said catheter until the distal tip thereof has reached the site, at which it is desired to collect debris;
b) inflating the balloon with expansion fluid;
c) pulling the inner conduit of said balloon catheter in a proximal direction, such that the distal and/or proximal end(s) of said balloon intussuscept(s);
d) deflating the balloon, thereby forming a cavity into which debris is collected and entrapped; and
e) removing the balloon catheter from the internal passage of the subject, together with the entrapped debris.

In one preferred embodiment of the presently-disclosed method, the aforementioned internal passage is a vein or artery.

In another aspect, the present invention further encompasses rapid exchange (RE) catheter implementations in which the length of a distal section of the catheter and the shape and/or volume of its distal balloon may be manipulated during procedures carried out therewith. Such implementations are ideally suited for use in debris collection applications, as described in connection with the OTW device of the present invention, hereinabove. However, the RE solutions of the present invention may also be used in any other RE application wherein it is necessary to alter the length of a distally-placed balloon element.

Consequently, the present invention is also directed to a rapid exchange catheter that permits axial movement of an inner conduit within an outer conduit comprising:

a) an outer conduit;
b) an inner conduit, suitable for total or partial passage over a guide wire, wherein said inner conduit is disposed within the lumen of said outer conduit such that the longitudinal axes of said inner and outer conduits are substantially parallel, wherein said inner conduit is capable of being moved along its longitudinal axis in relation to said outer conduit and wherein the proximal end of said inner conduit is angled such that it pierces the wall of said outer conduit;
c) means for permitting said axial movement of said inner conduit within said outer conduit, such that said movement is not hindered by the passage of the angled proximal part of the inner conduit through said outer conduit; and
d) means, situated at the proximal end of the outer conduit, for causing axial pushing-pulling movements of said inner conduit.

In one preferred embodiment of the above-defined rapid exchange catheter, the means for permitting unhindered axial movement of the inner conduit is provided by a sealing sleeve that is slidably fitted around the external conduit, such that the angled proximal portion of said inner conduit passes firstly through an elongated aperture in the wall of the external conduit, and secondly through a tightly sealed aperture in said sealing sleeve, such that upon axial movement of the inner conduit, said sealing sleeve is capable of preventing the transfer of fluid through said elongated aperture.

In another preferred embodiment, the above means for permitting unhindered axial movement of the inner conduit is provided by a two-part inner conduit construction, whereby the first, proximal part of said construction is non-movable, and wherein the second, distal part is slidably disposed within said proximal part.

In a further preferred embodiment, the abovementioned means for permitting unhindered axial movement of the inner conduit is provided by a two-part inner conduit construction, whereby the first, proximal part of said construction is non-movable, and wherein the second, distal part is slidably disposed over said proximal part.

In a still further preferred embodiment, the aforementioned means for permitting unhindered axial movement of the inner conduit is provided by a three-part inner conduit construction, whereby the first, proximal part of said construction is non-movable, and wherein the second, intermediate part is non-movably disposed within said proximal part, and wherein the third, distal part is slidably disposed within said intermediate part.

In another preferred embodiment of the rapid exchange catheter of the present invention, the means for causing axial movements of the inner conduit mentioned hereinabove comprise one or more wires, the distal end(s) thereof being attached to the inner conduit, and the proximal end(s) thereof extending beyond the proximal end of the outer conduit.

In another aspect, the present invention also provides a rapid exchange balloon catheter system comprising:

a) an outer conduit;
b) an inner conduit, suitable for total or partial passage over a guide wire, wherein said inner conduit is disposed within the lumen of said outer conduit such that the longitudinal axes of said inner and outer conduits are substantially parallel, wherein said inner conduit is capable of being moved along its longitudinal axis in relation to said outer conduit, wherein the proximal end of said inner conduit is angled such that it pierces the wall of said outer conduit, and wherein the distal tip of said inner conduit extends beyond the distal tip of said outer conduit;
c) an angioplastic balloon whose proximal margin is attached to the outer surface of the distal tip of said outer conduit, and whose distal margin is attached to the outer surface of the portion of the inner conduit that extends beyond the distal tip of said outer conduit, and wherein the distal and/or proximal end portion(s) of said balloon are capable of intussusception upon proximal movement of said inner conduit in relation to said outer conduit;
d) means, situated at the proximal end of the outer conduit, for causing axial pushing-pulling movements of said inner conduit;
e) means for the introduction of an expansion fluid into the annular space formed between the inner surface of the outer conduit and the outer surface of the inner conduit and therefrom into the lumen of said balloon, and for the removal thereof;
f) means for preventing pressure changes within said annular space upon axial movement of said inner conduit in relation to said outer conduit; and g) means for permitting axial movement of said inner conduit within said outer conduit, such that said movement is not hindered by the passage of the angled proximal part of the inner conduit through said outer conduit.

In one preferred embodiment of the rapid exchange balloon catheter system defined hereinabove, said system is constructed such that the distal portion of the balloon is capable of intussusception upon proximal movement of the inner tube in relation to the outer tube.

In one preferred embodiment of this aspect of the invention, the means for causing axial movements of the inner conduit comprise one or more wires, the distal end(s) thereof being attached to the inner conduit, and the proximal end(s) thereof extending beyond the proximal end of the outer conduit.

In another preferred embodiment of this aspect of the invention, the means for preventing pressure changes comprises a plunger slidably disposed within the proximal end of the outer conduit, wherein said plunger is connected to the axial pushing-pulling means, such that upon operation of said pushing-pulling means, said plunger is caused to slide either distally or proximally, thereby changing the volume of the outer conduit.

Any suitable means may be employed for permitting unhindered axial movement of the inner conduit in the above-defined rapid exchange balloon catheter system. Preferably, however, these means are as defined in any one of the preferred embodiments disclosed hereinabove and claimed hereinafter.

In particularly preferred embodiments of the RE catheter system of the present invention, the balloon shape and force resistance characteristics of the catheter tubing are as described hereinabove in connection with the OTW systems, and as exemplified in the Examples provided hereinbelow.

It should be noted that in each of the embodiments of the catheter systems of the present invention disclosed and described hereinabove, a lubricant (such as silicone oil or mineral oil) may be present in order to facilitate the mutual sliding of the various conduits.

In another aspect, the present invention also provides a method for collecting debris from an internal passage of a mammalian subject comprising the steps of:
a) inserting a rapid exchange balloon catheter system as defined hereinabove into said internal passage, and advancing said catheter until the distal tip thereof has reached the site, at which it is desired to collect debris;
b) inflating the balloon with expansion fluid;
c) pulling the inner conduit of said balloon catheter in a proximal direction, such that the distal and/or proximal end(s) of said balloon intussuscept(s);
d) deflating the balloon, thereby forming a cavity into which debris is collected and entrapped; and
e) removing the balloon catheter from the internal passage of the subject, together with the entrapped debris.

In one preferred embodiment of the presently-disclosed method, the aforementioned internal passage is a vein or artery.

All the above and other characteristics and advantages of the present invention will be further understood from the following illustrative and non-limitative examples of preferred embodiments thereof.

BRIEF DESCRIPTION OF THE DRAWINGS

The present invention is illustrated by way of example in the figures of the accompanying drawings, in which like references indicate similar elements and in which:

FIGS. 15A to 15C show longitudinal section views of a rapid exchange catheter according to a seventh preferred embodiment of the invention comprising a movable inner tube affixed to a slidable sealing sleeve.

DETAILED DESCRIPTION OF PREFERRED EMBODIMENTS

The present invention is directed to a method and apparatus for removing objects (such as atheromatous plaque debris) or collecting samples from a body passageway such as a blood vessel. The presently-disclosed method and apparatus may also be used to expand a region of a body passageway (such as an atheromatous narrowing or occlusion of a blood vessel) in addition to removing debris or other matter or objects therefrom. In a preferred embodiment of the invention, a balloon catheter that is suitable for carrying out common interventional procedures is adapted to enable the expansion of a region of a body passageway and collection of objects or samples from the treated site utilizing a unique design of catheter and balloon.

In the following description, the terms "conduit" and "tube" are used interchangeably.

Figure 1A:
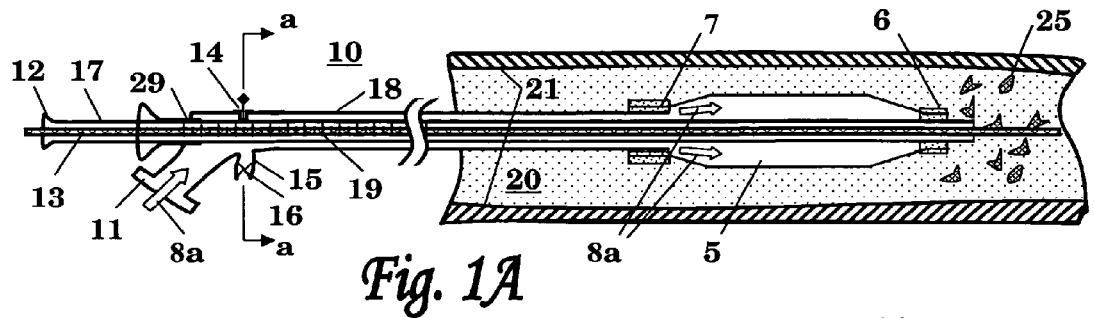
FIG. 1A schematically illustrates over-the-wire insertion of the balloon catheter of the invention.

Referring to FIG. 1A which illustrates the insertion of an OTW balloon catheter 10 of the invention to a treatment site, for example body passage 20. As shown, balloon catheter 10 comprises an inner tube 17 slidably positioned inside outer tube 18. The proximal (i.e., trailing) end of inner tube 17 comprises an entry port 12, which extends outwardly through orifice 29 provided at the proximal end of outer tube 18. Orifice 29 tightly fits around the outer surface of inner tube 17 without gripping it, thereby allowing proximal and distal movements of inner tube 17 while sealing the inner lumen of outer tube 18. Graduated scale 19 may optionally be provided on the outer surface of inner tube 17.

The proximal end of outer tube 18 further comprises a fluid port 11 for injecting/removing inflation fluids to/from inner lumen of outer tube 18, an over-pressure valve outlet 15 for discharging inflation fluids whenever over-pressure conditions develop in the inner lumen of outer tube 18, and an inner tube safety lock 14 adapted for gripping the outer surface of inner tube 17, thereby preventing proximal-distal movements thereof relative to outer tube 18.

Over-pressure valve outlet 15 may include an over-pressure valve 16 for sealing the opening of over-pressure valve outlet 15 and for discharging portions of inflating fluids therethrough whenever over-pressure conditions are reached in inner lumen of outer tube 18. It should be realized however that such over-pressure conditions may be resolved by other means. For example, an inflatable member (not shown) may be attached to the opening of over-pressure valve outlet 15, and in such an implementation over-pressure valve 16 may be eliminated. Moreover, outer tube 18, or portions thereof, may be inflatable such that over-pressure conditions may be resolved by its expansion.

Figure 1B:
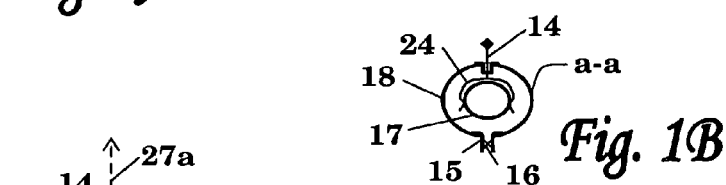
FIG. 1B shows a cross sectional side view of the balloon catheter of the invention.

Inner tube safety lock 14 contacts the outer surface of inner tube 17 via a tight orifice provided on the outer surface at the proximal end of outer tube 18. As shown in the cross sectional view of FIG. 1B, a "U"-shaped gripping clip 24 may be attached to inner tube safety lock 14 for gripping inner tube 17 therewith by pushing inner tube safety lock 14 inwardly and fitting the arms of gripping clip 24 around the outer surface of inner tube 17.

As seen in FIG. 1A distal (leading) end of inner tube 17 extends outwardly via the distal opening of outer tube 18, into the body passage 20. An inflatable member, for example non-compliant balloon 5, is attached to the distal ends of outer tube 18 and inner tube 17. Balloon 5 is preferably made from a flexible resilient sleeve having conical ends having gradually decreasing diameters towards the tips of the sleeve. Balloon 5 is attached at circumferential attachment point 7 to the outer surface near the distal tip of outer tube 18, and at circumferential attachment point 6 to the outer surface near the distal tip of inner tube 17, such that it seals the distal opening of outer tube 18.

Figure 1C:
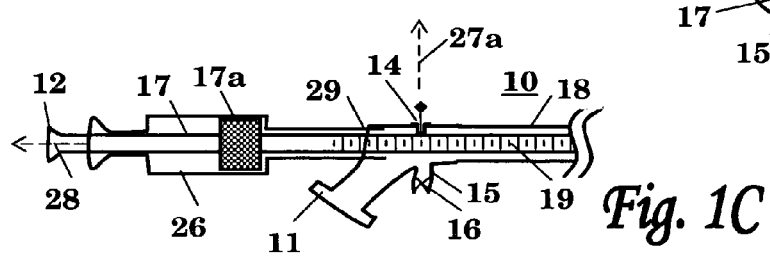
FIG. 1C schematically illustrates one embodiment of the syringe-like pressure-compensating device situated at the proximal end of the catheter system.

As mentioned hereinabove, in one preferred embodiment of this aspect of the invention, the means for preventing pressure changes in the inflation fluid space comprises a syringe-like structure positioned at the proximal end of the catheter system, wherein the barrel of said syringe-like structure is formed by an expanded portion of the outer conduit, and wherein the plunger of said structure co-axially surrounds the proximal end of the inner conduit. Referring now to FIG. 1C, the mechanism in this preferred embodiment consists of a barrel portion 26 and plunger 17*a* movably disposed therein and affixed to outer surface of inner tube 17. Plunger 17*a* seals the inflation lumen of balloon catheter 10, such that proximal movements thereof, responsive to proximal movements of inner tube 17, generate suction of inflation media into barrel portion 26.

Figure 3:
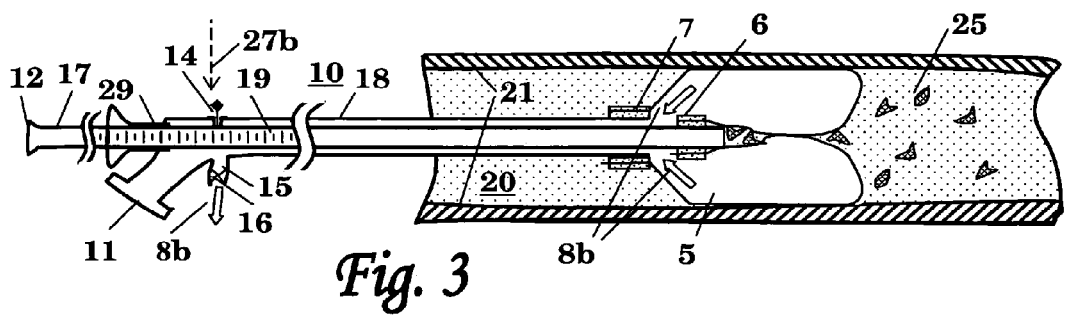
FIGS. 3 and 4 schematically illustrate debris collection carried out by the balloon catheter of the invention by folding the inflated balloon and deflating it thereafter.

With reference to the flowchart of FIG. 3, demonstrating the steps of an interventional procedure performed with an OTW balloon catheter of the invention. The procedure starts in step 50 wherein the balloon catheter 10 is guided to the treatment site (e.g., over the wire). FIG. 1A demonstrates over-the-wire insertion, wherein the insertion of balloon catheter 10 is performed over guide wire 13. It should be clear, however, that the invention is not limited to one specific insertion method and that other appropriate and practicable insertion methods (e.g., using a guiding catheter) may also be used.

Next, in step 51, the operator inflates balloon 5 by injecting inflation fluids via fluid port 11 and the inner lumen of outer tube 18, as demonstrated by fluid inflation arrows 8*a* in FIG. 1A. When carrying out procedures in body passage 20 as demonstrated in the FIGS. 1-4 inflation fluids are preferably injected into balloon 5 such that its circumferential sides are expanded and pressed against the inner wall 21 of body passage 20, as demonstrated in FIG. 2. The pressure inside balloon 5 in such conditions may be in general about 1-25 Atmospheres, preferably about 6 Atmospheres.

In this state in which the balloon catheter 10 is anchored, the inner lumen of inner tube 17 may now be utilized for operating in the treated site with different interventional tools (not shown), as may be required. Step 52 indicates the possibility of performing procedures if needed, however, some procedures (for example angioplasty) may be completed, or be near completion, once balloon 5 reaches its inflated state.

Figure 2:
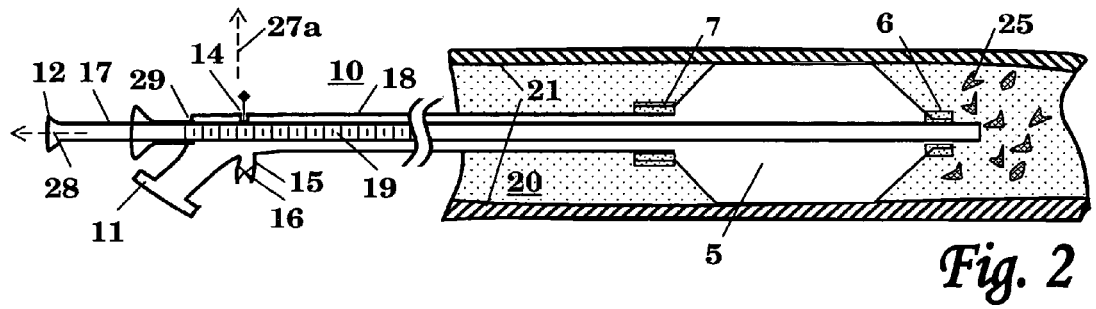
FIG. 2 schematically illustrates the balloon catheter of the invention when inflated at a treatment site.

If it is determined in step 53 that a sample or other liquid or solid matter should be collected from the treatment site, for example fluids, secretions, and/or debris 25, then in step 54 inner tube safety lock 14 is pulled thereby releasing its grip from inner tube 17, as demonstrated by arrow 27*a* in FIG. 2. In step 55 the inner tube 17 is retracted outwardly (proximally) by the operator as shown by arrow 28. During retraction of inner tube 17 the distal tip of balloon 5 collapses and the outer surface portions are folded inwardly over the distal tip of inner tube 17 and thereafter over itself as further portions of the balloon collapse, as illustrated in FIG. 3.

Retraction of inner tube 17 and the resulting inward folding of balloon 5 shorten the overall length of inflated balloon 5 which actually reduces the volume of inflated balloon 5. Consequently, the pressure exerted by the inflating fluids increases, resulting in a considerable pressure increase in balloon 5 and inner lumen of outer tube 18. Whenever the pressure in balloon 5 and inner lumen of outer tube 18 reaches a certain set-point, inflation fluids are discharged via over-pressure valve outlet 15, as shown by arrows 8*b* in FIG. 3, such that the pressure in balloon 5 and inner lumen of outer tube 18 remains within a predetermined pressure range (e.g., 1-25 atmospheres). During this step the operator can determine via graduated scale 19 the amount of length of inner tube 17 that has been retracted and in this way determine when to stop the retraction and prevent further axial movement of inner tube 17 (step 58) by pushing down inner tube safety lock 14, as indicated by arrow 27*b*.

Figure 4:
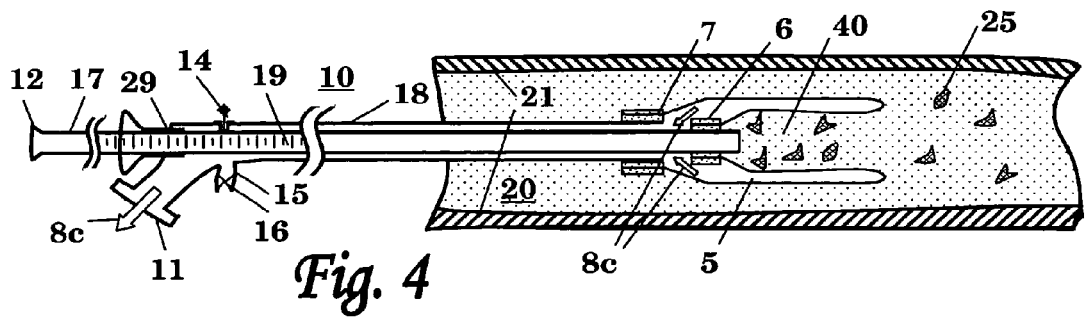
Figure 5:
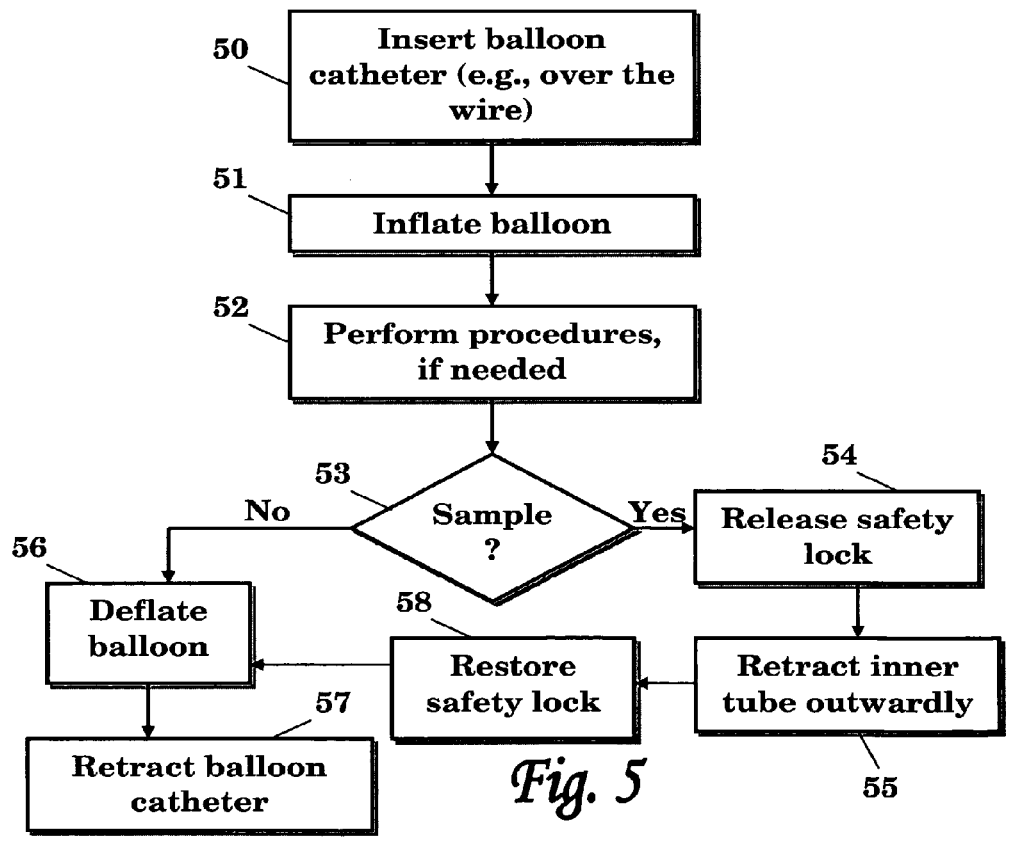
FIG. 5 is a flowchart demonstrating the steps of an interventional procedure performed with the balloon catheter of the invention that may involve sample collection.

Next, in step 56, balloon 5 is deflated by retracting inflation fluids via fluid port 11, as indicated by arrows 8*c* in FIG. 4. In result, the pressure inside balloon 5 and inner lumen of outer tube 18 is substantially decreased, and balloon 5 is deflated. The reduction in the volume of balloon 5 results in the formation of an inner cavity 40 defined by the outer surface of the folded balloon section, as shown in FIG. 4. The cavity 40 is formed such that when the intussuscepted balloon 5 is deflated, the cavity 40 is enlarged, trapping therewithin debris and/or particulate matter without the need for application of externally applied suction. In step 57 the operator retracts balloon catheter 10 proximally such that portion of fluid/secretion and debris 25 confined within inner cavity 40 are withdrawn with the balloon catheter 10 (not shown in the figures). The debris, objects or samples collected may be easily collected when the entire length of balloon catheter 10 is ejected from the body of the treated subject, by pushing the inner tube 17 distally and unfolding the folded portions of balloon 5, thus restoring the deflated state of balloon 5 (shown in FIG. 1A).

In view of the axially-directed stretching and buckling forces exerted on the inner and outer tubes during elongation and shortening of the balloon, said tubes need to be constructed such that they are able to withstand axially-directed forces in the range of between 2 and 20 Newton without undergoing deformation. In order to achieve this aim, the conduits may be constructed of a braided material or of materials having a defined molecular orientation. The approximate maximum forces that the inner and outer tubes need to withstand (for two difference size ranges of balloon) are as follows:

2.5-4 mm balloons: the tubing should withstand up to 500 g; polymer tubing made of nylon or pevax reinforced during the manufacturing process can be used.

4-5 mm (or larger) balloons: the tubing should withstand forces up to 2 kg. In this case it will be necessary to use a braided tube (polymer tube with metal mesh reinforcement).

Results for a representative study of the forces generated during balloon folding are presented in Example 2, hereinbelow.

Outer tube 18 is preferably made from a biocompatible polymer type of material, such as polyurethane or nylon or PET, and may be manufactured utilizing conventional methods, such as extrusion. The diameter of inner lumen of outer tube 18 is generally in the range of 0.5-2.0 mm (millimeters), preferably about 0.7 mm, and the diameter of fluid port 11 is generally in the range of 2-6 mm, preferably about 4 mm. The diameter of over-pressure valve outlet 15 is generally in the range of 1-6 mm, preferably about 4 mm, and the entire length of outer tube 18 is generally in the range of 100-2000 mm, preferably about 1400 mm.

Inner tube 17 is preferably made from a biocompatible polymer type of material, such as polyurethane or nylon or PET, and it may be manufactured utilizing conventional methods, such as extrusion. The diameter of inner lumen of inner tube 17 is generally in the range of 0.2-2.0 mm, preferably about 0.5 mm, and its entire length is generally in the range of 100-2000 mm, preferably about 1500 mm.

While the diameter of orifice 29 provided at the proximal tip of outer tube 18 should be adapted to provide appropriate sealing of inner lumen of outer tube 18 it should also close over the outer surface of inner tube 17 such that inner tube 17 may be displaced therethrough with relatively low frictional forces. For example, if the diameter of inner tube 17 is 0.7 mm, then the diameter of orifice 29 should be 1.0 mm.

Balloon 5 is preferably a non-compliant or semi-compliant balloon such as manufactured by Advanced Polymers (Salem, USA) and by Interface Associates (CA). It may be manufactured utilizing conventional methods known in the balloon catheter industry from a non-compliance type of material such as Pebax or Nylon (preferably Nylon 12). Its length is generally in the range of 10-60 mm, preferably about 20 mm. The body diameter can vary from 2.0 mm to 5 mm for coronary artery applications, and be significantly larger for use in larger blood vessels. Preferably, the balloon should have a burst pressure within the range of 12-20 atmospheres. The proximal and distal edges of balloon 5 are preferably adhered to the outer surfaces of outer tube 18 and inner tube 17 respectively, at circumferential attachment points 7 and 6 respectively, by utilizing a UV or thermo-bonding type of adhesive such as commonly used in the art.

The shape of balloon 5 has been found by the present inventors to be critical in order for said balloon to fulfill its intended functions in the presently disclosed and claimed catheter system, namely:
 i. to facilitate folding in such a way that the desired annular space is formed at the distal end of the intussuscepted balloon, by the application of the lowest possible retracting force;
 ii. to present a low profile that will facilitate introduction and withdrawal of the deflated balloon into and out of the catheter system and body passage.

The materials and design of the balloon, especially the shape of the distal taper and the relationship between the distal and the proximal taper, thus allow the balloon to fold smoothly and with relatively low pulling forces. This also insures that the balloon will fold only its distal side.

It appears, from modeling studies performed by the inventors, that a tapered balloon with a smooth round ending folds best and has a relatively low retracting force, when compared to standard tapered balloon or a balloon with a round ending. In a particularly preferred embodiment, the balloon has a proximal taper cone shaped with a 15-17 degree angle, and a 15 degree round cone distal taper, having a radius of about 0.5 mm at the junction of the taper and the neck. The results of the aforementioned modeling studies are presented in Example 2, hereinbelow.

Inner tube safety lock 14 is preferably made from a biocompatible polymer such as Tecoflex; its length is generally in the range of 1-15 mm, preferably about 5 mm. If, for example, the cross-sectional diameter of inner tube safety lock 14 is about 2 mm, then the orifice provided on the outer surface of outer tube 18 through which inner tube safety lock 14 accesses inner lumen of outer tube 18 is preferably about 2.4 mm for providing suitable sealing of inner lumen of outer tube 18.

In another aspect, the present invention aims to provide rapid exchange (RE) catheter implementations in which the length of a distal section of the catheter and the shape and/or volume of its distal balloon may be manipulated during procedures carried out therewith. Such implementations are ideally suited for use in debris collection applications, as described in connection with the OTW device of the present invention, hereinabove. However, the RE solutions of the present invention may also be used in any other RE application wherein it is necessary to alter the length of a distally-placed balloon element.

In general, the RE catheter of the invention comprises an outer catheter shaft and an inner tube provided therein, wherein the lumen of said inner tube may be accessed via a lateral port provided on the catheter's shaft. In some of the preferred embodiments of the present invention described herein the inner tube of the catheter is affixed to the catheter's outer shaft and the catheter's length and its balloon are manipulated by a unique construction of the inner tube. In these constructions the catheter's inner tube may comprise a slidable distal tube that may be moved by the operator, distally or proximally relative to the catheter's outer shaft, via a displacement rod attached thereto. Alternatively, the inner tube may be encompassed in a slidable intermediate tube which may be moved by the operator distally or proximally relative to the catheter's shaft.

In further embodiments of the invention a unique catheter construction is developed in order to provide a movable inner tube affixed to a slidable sealing sleeve which allows the operator to move the inner tube distally or proximally relative to the catheter's outer shaft and thereby manipulate its length and balloon.

FIG. 9 shows longitudinal section views of a first embodiment of the rapid exchange catheter 610 of the invention wherein the distal end of the catheter's inner tube 614 comprises a slidable internal tube 613. Catheter 610 comprises a hollow outer shaft 66 comprising inner tube 614 installed therein, and a slidable internal tube 613 placed in inner tube 614 such that it protrudes distally via a distal opening thereof. In this construction the inner lumens of inner tube 614 and slidable internal tube 613 are linked, thereby providing a continuous inner lumen ending at a distal opening of slidable internal tube 613. Proximal end of balloon 611a is attached to hollow outer shaft 66 at proximal attachment points 62b provided around the outer surface of a distal section thereof, and the distal end of said balloon is attached to the slidable internal tube 613 at distal attachment points 62a provided around the outer surface of a distal section of said slidable internal tube.

The lumen of inner tube 614 may be accessed via a lateral port 612 provided on hollow outer shaft 66, between a distal and proximal ends thereof. Guide wire 65 (or other suitable accessories) may be inserted via lateral port 612, advanced along the inner lumens of inner tube 614 and slidable internal tube 613, and exit the inner lumen of slidable internal tube 613 through a distal opening thereof.

Slidable concentric member 613 is adapted to fit into inner tube 614 and its diameter is preferably smaller than the diameter of inner tube 614 such that it seals its distal opening while comfortably permitting distal or proximal sliding of slidable internal tube 613 therethrough. Distal end portion of displacement rod 618 is attached to slidable internal tube 613 thereby allowing the operator to move slidable internal tube 613 distally or proximally relative to the catheter's outer shaft by pushing or pulling the proximal tip of displacement rod 618.

Further sealing of the distal opening of inner tube 614 may be achieved by an annular gasket 64 attached to the surface of distal tip of inner tube 614 such that a distal portion thereof is pressed against an annular portion of the outer surface of slidable internal tube 613.

The proximal portion of hollow shaft 66 comprises a fluid port 617 used for inflating or deflating balloon 611a by an inflation fluid pressurized therethrough, an optional discharge valve 616 installed in discharge valve outlet 615, and rod aperture 619 for moving displacement rod 618 distally or proximally therethrough.

During a typical procedure RE catheter 10 is inserted into a body treatment site in which balloon 611a may be inflated by an inflation fluid (designated by arrows 67a in FIG. 9A) pressurized through inflation fluid port 617, for effecting dilation or other procedures in said treatment site and/or for anchoring said balloon therein. The pressurized fluids pass via the hollow interior of hollow shaft 66 and reach the interior of balloon 611a via a distal opening thereof. In its inflated state, shown in FIG. 9B, the hollow interior of hollow shaft 66 and the internal space of balloon 611a are filled with pressurized inflation fluid. Distal opening of inner tube 614 is sealed by slidable internal tube 613 and (optionally) by gasket 64, thereby preventing leakage of pressurized inflation fluid thereinto. The pressure of the inflation fluid inside the system presses the gasket and improves the sealing provided by gasket 64. On the other hand, when the pressure of the inflation fluid is reduced the gasket's grip on the outer surface of inner tube 614 is diminished which makes it easier for the gasket to slide over it.

The requisite procedure is typically carried out in the inflated state of the balloon. By using the catheter of the invention for such procedures the operator may manipulate the catheter length and the shape and volume of balloon 611a by pulling displacement rod 618b, thereby moving slidable internal tube 613 proximally further into inner tube 614, as demonstrated by arrows 68a. In result, the distal end of balloon 611a collapses and folds internally, as shown in FIG. 9C, which increases the pressure of the inflation fluid. Whenever the pressure of the inflation fluid inside the hollow interior of hollow outer shaft 66 and in balloon 611a is above a predetermined threshold value a slender passage of discharge valve is expanded to allow portions of inflation fluid to exit via discharge valve outlet 615 and thereby reduce the pressure of inflation fluid below said threshold value.

It should be noted that the use of pressure discharge elements 615 and 616 constitutes merely one possible means of pressure reduction.

Hollow outer shaft 66 is preferably made from a polymer or metal material, such as stainless steel (e.g. stainless steel 316), nitinol, or nylon, and it may be manufactured utilizing conventional methods, such as extrusion and laser cutting. The diameter of the hollow interior of hollow shaft 66 is generally in the range of 1-2 mm (millimeters), preferably about 1.2 mm, and the diameter of inflation fluid port 617 is generally in the range of 2-6 mm, preferably about 3 mm. The diameter of discharge valve outlet 615 is generally in the range of 2-6 mm, preferably about 3 mm, and the entire length of hollow shaft 66 is generally in the range of 500-2000 mm, preferably about 1400 mm.

Inner tube 614 is preferably made from a flexible polymer or metal material, such as pevax, nylon, stainless or nitinol and it may be manufactured utilizing conventional methods, such as extrusion and laser cutting. The diameter of inner lumen of inner tube 614 is generally in the range of 0.3-1 mm, preferably about 0.8 mm, and its entire length is generally in the range of 100-300 mm, preferably about 120 mm. Slidable internal tube 613 is preferably made from a flexible polymer or metal type of material, such as pevax, nylon, stainless or nitinol, and it may be manufactured utilizing conventional methods (e.g. extrusion). The diameter of inner lumen of slidable internal tube 613 is generally in the range of 0.3-1 mm, preferably about 0.5 mm, and its entire length is generally in the range of 30-150 mm, preferably about 70 mm.

Balloon 611a is preferably a type of non-compliant or semi-compliant or low-compliant balloon such as manufactured by Interface Associates. It may be manufactured utilizing conventional methods known in the balloon catheter industry from a biocompatible polymer type of material such as nylon 12. Its length is generally in the range of 5-50 mm, preferably about 20 mm, and its diameter is generally in the range of 2 to 12 mm, preferably about 3 to 5 mm. The proximal and distal edges of balloon 611a are preferably adhered to the outer surfaces of hollow shaft 66 and slidable internal tube 613, at circumferential attachment points 62b and 62a respectively, by utilizing a low profile type of adhesion such as thermo bonding, UV adhesives or acrylic manufactured by Locktight.

Displacement rod 618 may be manufactured from a metal wire or tube, such as Stainless steel, Nitinol (Nickel Titanium) and polymers, having a diameter generally in the range of 0.2-2 mm, preferably about 0.5 mm, and length generally in the range of 500-2000 mm, preferably about 1600 mm. Distal portion of displacement rod 618 may be adhered to the distal section of slidable internal tube 613. Most preferably, distal portion of displacement rod 618 may be combined into the wall of internal tube 613 thereby enhancing its rigidity and the grip provided therewith. Rod aperture 619 is adapted to allow conveniently moving displacement rod 618 therethrough while providing suitable sealing of the hollow interior of hollow shaft 66, thereby preventing leakage of inflation fluid therefrom.

The inflation fluid is preferably a saline or a saline mixed with radio-opaque solution in different ratios. A syringe pump, or other suitable inflation pumps, as commonly used in the field, may be used for introducing the inflation fluid into the system. The pressure in the system in its various states is typically in the range of 1 to 25 atmospheres.

While different discharge valves may be employed, discharge valve 616 is preferably implemented by an annular element having an axial slender passage passing therein. In such implementation discharge valve 616 is manufactured from an elastomer type of material, such as PVC by an injection molding process. Its outer diameter is generally in the range of 2-6 mm, preferably about 4 mm, and its slender passage is designed to expand whenever a pressure gradient of about 4 atmospheres evolves between its ends.

Figure 9A:
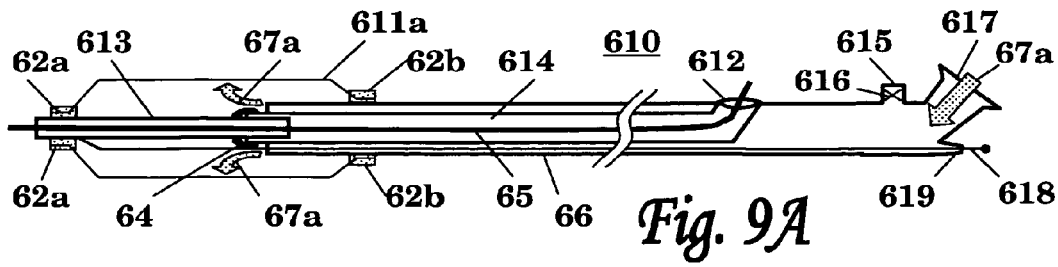
FIGS. 9A to 9C show longitudinal section views of a rapid exchange catheter according to one preferred embodiment of the invention wherein the distal section of the inner tube comprise an internal slidable tube.
Figure 9B:
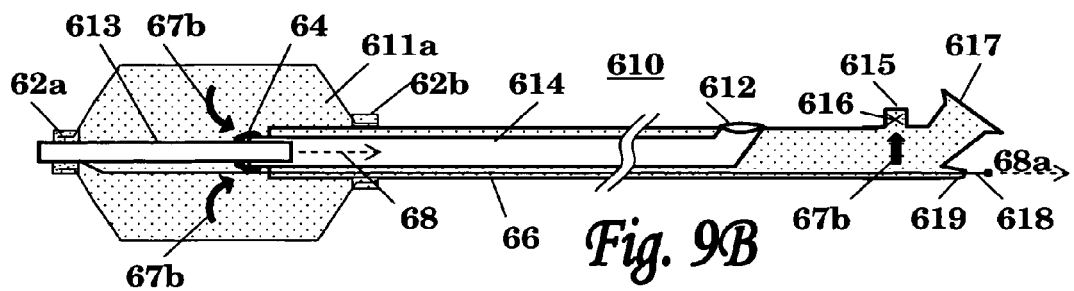
Figure 9C:
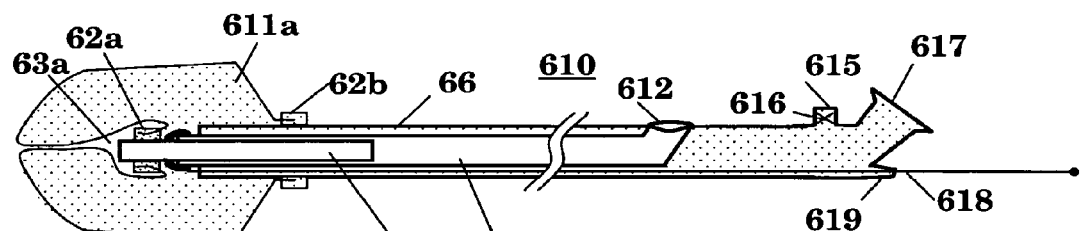
Figure 9D:
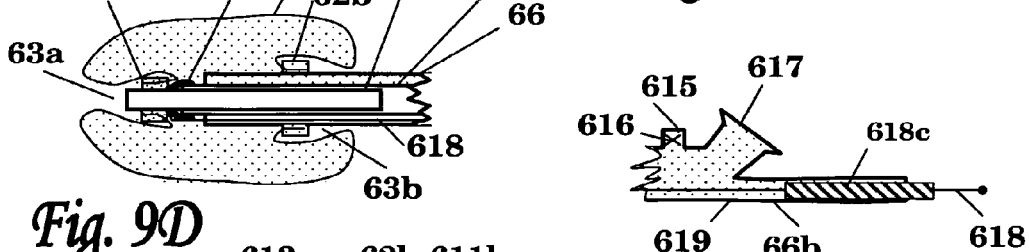
FIGS. 9D and 9E demonstrate utilizing different balloons for different manipulations thereof.
Figure 9F:
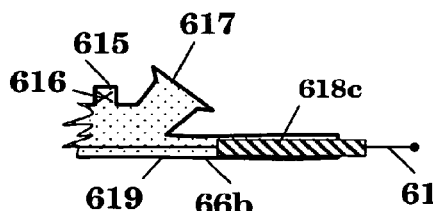
FIG. 9F demonstrates a piston-like construction for preventing pressure accumulation within the catheter during retraction.

Optionally, a proximal part 618c of rod 618 is made to be wide enough to occupy a volume of space within a proximal portion 66b of hollow shaft 66, as sown in FIG. 9F. This piston-like construction 618c allows for a syringe like action of rod 618 when retracted proximally, causing it to evacuate enough space in the proximal portion 66b of the lumen of hollow shaft 66. This extra space will then be filled by inflation fluid, thereby preventing pressure build-up within the catheter during retraction of the rod 618.

As shown in FIG. 9C in its folded state distal cavity 63a is obtained by the inwardly folded distal sections of balloon 611a. The volume encompassed by cavity 63a may be enlarged by (partially or entirely) deflating the balloon in this folded state, thereby filling the enlarged cavity with samples and/or debris from the treatment site. Different distal balloons may be designed to provide various balloon manipulations as exemplified in FIGS. 9D and 9E.

Figure 9E:
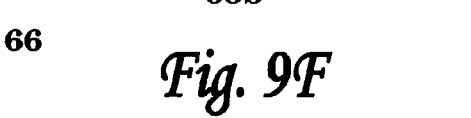

For example, in balloon 611b shown in FIG. 9E a proximal section of the balloon collapses and folds inwardly in response to movement of slidable internal tube 613 proximally, thereby forming a proximal cavity 63b. Such a result may be achieved by using a balloon which has higher resistance to folding at its proximal tapered end relative to its distal tapered end This can be achieved by using a balloon having different angles at its distal and proximal tapers, wherein a steeper taper facilitates its folding.

As another example, in balloon 611ab shown in FIG. 9D both, proximal and distal, sections of the balloon are folded in response to movement of slidable internal tube 613 proximally, thereby forming a proximal cavity 63b and a distal cavity 63a. This result may be obtained for example by using a balloon 611ab with a symmetric shape—namely, the balloon having the same taper at its distal and proximal sides.

The procedure for using the RE balloon catheter of the present invention may be briefly described as follows:

1) Insertion of catheter into the body via peripheral blood vessel by use of standard rapid exchange method, as is well known in the art;
2) Inflation of the balloon by injecting inflation fluids via fluid port 617 and the inner lumen of outer shaft 66, as demonstrated by fluid inflation arrows 67a in FIG. 9A; the Pressure inside balloon 611 may be in general about 1-25 Atmospheres, preferably about 6 Atmospheres.
3) If required, a sample or other liquid or solid matter (for example fluids, secretions, and/or debris) may be collected from the treatment site. Firstly, the safety lock mechanism fitted to the proximal end of proximal displacement rod 618 is pulled, thereby releasing its grip on said proximal displacement rod. (The safety lock is not shown in FIG. 9A; a suitable type of safety mechanism is, however, depicted in FIG. 13 and described—in relation to the OTW device of the present invention—hereinabove.) Displacement rod 618 is then pulled proximally, thereby releasing retracting slidable internal tube 613 proximally, as demonstrated by arrow 68a in FIG. 9B. During retraction of slidable internal tube 613 by the operator the distal tip of balloon 611 collapses and its outer surface portions are folded inwardly over the distal tip of slidable internal tube 613 and thereafter over itself as further portions of the balloon collapse, as illustrated in FIG. 9C.
4) Retraction of slidable internal tube 613 and the resulting inward folding of balloon 611 shortens the overall length of inflated balloon 611 which actually reduces the volume of inflated balloon 611. Consequently, the pressure exerted by the inflating fluids increases, resulting in a considerable pressure increase in balloon 611 and inner lumen of outer shaft 66. Whenever the pressure in balloon 611 and inner lumen of outer shaft 66 reaches a certain set-point inflation fluids can be discharged via discharge valve 616, as shown by arrows 67b in FIG. 9B, such that the pressure in balloon 611 and inner lumen of outer shaft 66 remains within a predetermined pressure range (e.g., 1-25 atmospheres). Another exemplary option for discharging pressure is by widening the proximal section 618c of rod 618 so it can act similar to a syringe action, as shown in FIG. 9F. During this step the operator can determine via graduated scale (not shown) provided on rod 618 the amount of length of inner tube 614 that has been retracted and in this way determine when to stop the retraction of inner tube 614. The aforementioned safety lock is then returned to its locked state, thereby preventing any further movement of displacement rod 618 and inner tube 614.
5) Subsequently, balloon 611 is deflated by retracting inflation fluids via fluid port 617. As a result, the pressure inside balloon 611 and inner lumen of outer tube 66 is substantially decreased, and balloon 611 is deflated. The reduction in the volume of balloon 611 results in enlargement of distal cavity 63a.
6) The operator then retracts balloon catheter 610 proximally such that portion of fluid/secretion and debris confined within proximal cavity 63a are withdrawn with the balloon catheter 610 (not shown in the figures).

The debris, objects or samples collected may be easily collected when the entire length of balloon catheter 610 is ejected from the body of the treated subject, by pushing the inner tube 614 distally and unfolding the folded portions of balloon 611, thus restoring the deflated state of balloon 611 (shown in FIG. 9A).

Figure 10A:
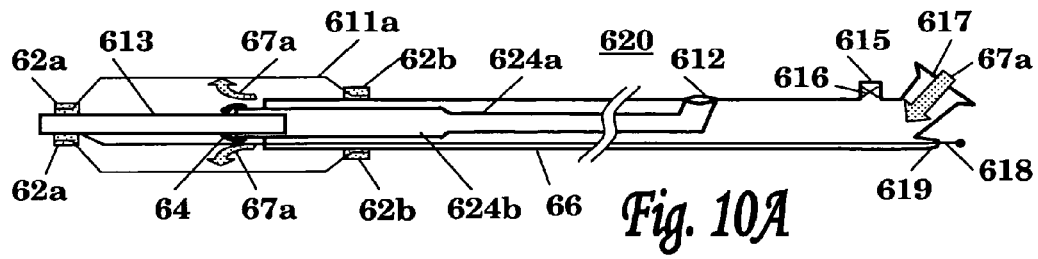
FIGS. 10A to 10C show longitudinal section views of a rapid exchange catheter according to a second preferred embodiment of the invention wherein the diameter of the distal section of the inner tube is adapted to receive an internal slidable tube.
Figure 10B:
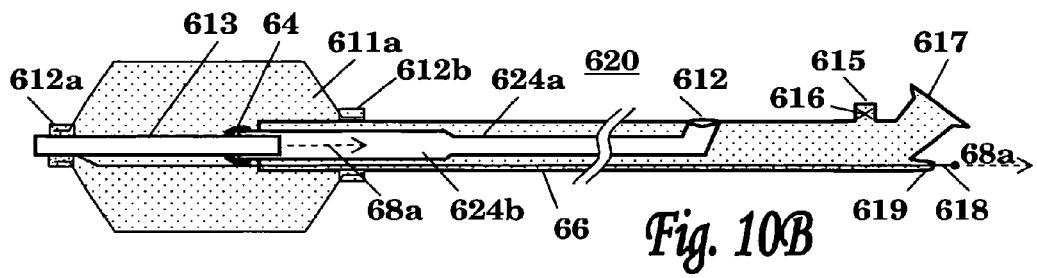
Figure 10C:
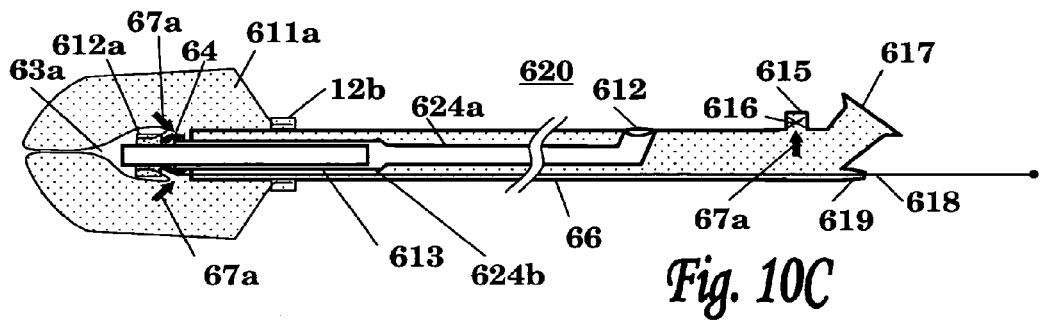

FIGS. 10A to 10C show longitudinal section views of a rapid exchange catheter 620 according to a second preferred embodiment of the invention wherein the diameter of a distal section 624b of the inner tube 624a is adapted to receive internal slidable tube 613. In this preferred embodiment the diameter of distal section 624b of inner tube 624a is made relatively greater than the diameter of the proximal section thereof. Internal slidable tube 613 is designed to tightly fit into proximal section 624b and thereby seal its distal opening and prevent leakage of inflation fluid thereinto. Alternatively or additionally, sealing may be achieved by gasket 64 attached to the distal section 624b of inner tube 624a such that a distal portion thereof is pressed against an annular portion of the outer surface of slidable internal tube 613. Internal slidable tube 613 and the proximal section of inner tube 624a may be manufactured to have the same inner diameter, thereby forming a substantially homogenous inner lumen therebetween, particularly when internal slidable tube 613 is advanced all the way into distal section 624b.

The structure and geometrical dimensions of elements of catheter 620 are much the same as those elements designated by the same numerals which were described above with reference to FIGS. 9A to 9C. Similarly, balloon 611a may be inflated by inflation fluid (67a) pressurized via inflation fluid port 617, and catheter's 620 length and the shape and volume of balloon 611a may be manipulated by moving displacement rod 618 distally or proximally, as exemplified in FIGS. 10A to 10C. Different balloons may be designed to provide various balloon folding configurations as exemplified in FIGS. 9D and 9E.

Inner tube 624a may be manufactured by an extrusion and laser cutting process from a plastomeric or metallic type of material, preferably from nylon, PET or stainless steel. The diameter of the distal section of inner tube 624a is generally in the range of 0.3-2 mm, preferably about 0.5 mm, and the diameter of slidable internal tube 613 is adapted to provide tight fitting and the necessary sealing of distal opening of inner tube 624a when said internal tube is inserted thereinside.

Figure 11:
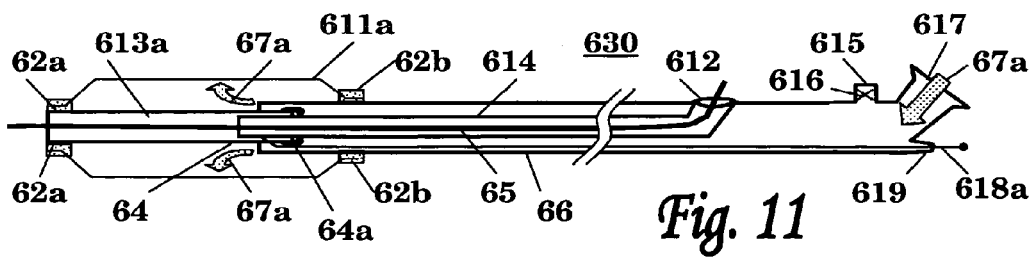
FIG. 11 shows a longitudinal section view of a rapid exchange catheter according to a third preferred embodiment of the invention wherein the distal section of the inner tube comprise an external slidable tube.

FIG. 11 shows a longitudinal section view of catheter 630 according to a third preferred embodiment of the invention wherein the distal section of the inner tube 614 comprises an external slidable tube 613a. In this preferred embodiment the distal end of balloon 611a is attached to the slidable external tube 613a at distal attachment points 62a provided around the outer surface of a distal section of said slidable external tube. The diameter of external slidable tube 613a is made relatively greater than the diameter of inner tube 614. External slidable tube 613a is designed to tightly fit over the outer surface of the proximal section of inner tube 614 and to thereby seal its distal opening and prevent leakage of inflation fluid thereinto. Alternatively or additionally, sealing may be achieved by gasket 64 attached to the proximal end portion of external slidable tube 613a such that a proximal portion thereof is pressed against an annular portion of the outer surface of inner tube 614.

Using such external slidable tube 613a in catheter 630 allows attaching a relatively shorter displacement rod 618a to the proximal section of said slidable tube 613a. Alternatively or additionally, the distal portion of displacement rod 618a may be combined into the wall of external slidable tube 613a along its longitudinal length, thereby enhancing its rigidity and the grip provided therewith.

The structure, geometrical dimensions of elements of catheter 630 designated by the same numerals, and the method of manipulating its length and balloon's volume and shape, are much the same as those elements and manipulating method which were previously described hereinabove and therefore, for the sake of brevity, said elements will not be further discussed at this point. External slidable tube 613a may be manufactured by an extrusion and laser cutting process from a plastomeric or metallic type of material, preferably from nylon or stainless steel. The diameter of external slidable tube 613a is adapted to provide tight fitting and the necessary sealing of distal opening of inner tube 614 when said external slidable tube is mounted thereover. For example, the diameter of external slidable tube 613a may be in the range of 0.3-2 mm, preferably about 0.8 mm.

Figure 12:
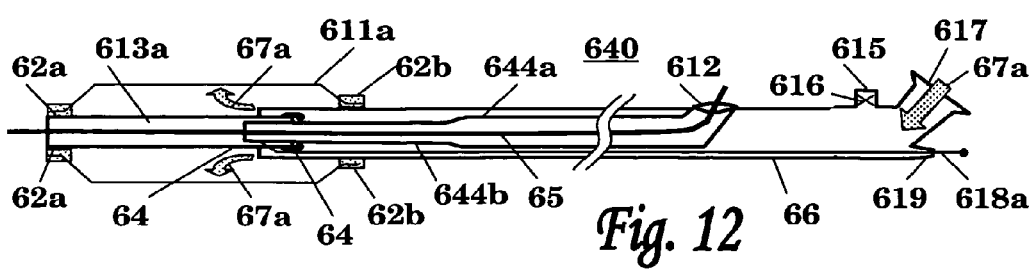
FIG. 12 shows a longitudinal section view of a rapid exchange catheter according to a fourth preferred embodiment of the invention wherein the diameter of the distal section of the inner tube is adapted to be received in an external slidable tube.

A fourth preferred embodiment (640) of the invention is demonstrated in the longitudinal section view shown in FIG. 12, wherein the diameter of the distal section 644b of inner tube 644a is adapted to be received in an external slidable tube 613a. In this preferred embodiment the distal end of balloon 611a is attached to the slidable external tube 613a at distal attachment points 62a provided around the outer surface of a distal section of said slidable external tube. The diameter of distal section 644b of inner tube 644a is made relatively smaller than the diameter of the proximal section thereof. External slidable tube 613a is designed to tightly fit over proximal section 644b and thereby seal its distal opening and prevent leakage of inflation fluid thereinto. Alternatively or additionally, sealing may be achieved by gasket 64 attached to the proximal end of External slidable tube 613a such that a proximal portion thereof is pressed against an annular portion of the distal section 644b of inner tube 644a.

The external slidable tube 613a of catheter 640 allows attachment of a relatively shorter displacement rod 618a to the proximal section of said slidable tube 613a. Alternatively or additionally, the distal portion of displacement rod 618a may be combined into the wall of external slidable tube 613a along its longitudinal length, thereby enhancing its rigidity and the grip provided therewith.

The structure, geometrical dimensions of elements of catheter 640 designated by the same numerals, and the method of manipulating of its length and balloon's volume and shape, are much the same as those elements and the manipulating method which were previously described hereinabove and therefore will not be further discussed here. Inner tube 644a may be manufactured by an extrusion and laser cutting process from a plastomeric or metallic type of material, preferably from nylon or stainless steel. The diameter of the distal section 644b of inner tube 644a is generally in the range of 0.3-2 mm, preferably about 0.3 mm, and the diameter of external slidable tube 613a is adapted to provide tight fitting and the necessary sealing of distal opening of inner tube 644a when said external tube is mounted thereover.

Figure 13:
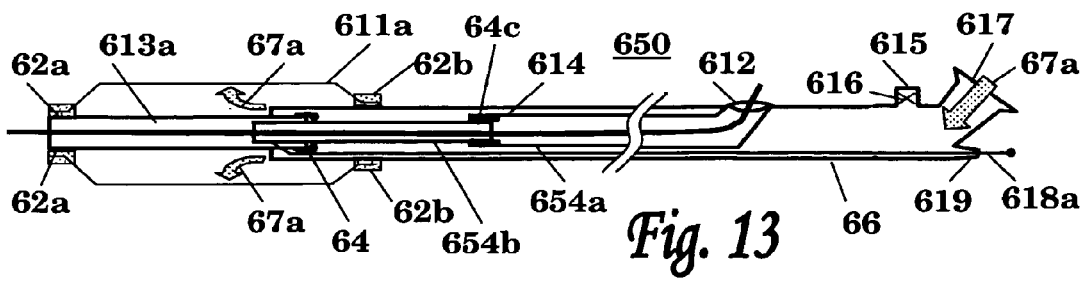
FIG. 13 shows a longitudinal section view of a rapid exchange catheter according to a fifth preferred embodiment of the invention wherein the distal section of the inner tube comprises a fixed inner tube on which an external slidable tube is mounted.

In a fifth preferred embodiment of the invention, illustrated in the longitudinal section view shown in FIG. 13, an external slidable tube 613a is mounted over a inner tube 654b protruding distally through a distal opening of fixed inner tube 654a of catheter 650. In this preferred embodiment the distal end of balloon 611a is attached to the slidable external tube 613a at distal attachment points 62a provided around the outer surface of a distal section of said slidable external tube. A proximal end portion of fixed inner tube 654b is fitted into a distal opening of inner tube 654a, such that it seals said distal opening and most of its longitudinal length protrudes distally therefrom into the hollow interior of hollow shaft 66. The diameter of external slidable tube 613*a* is adapted to tightly fit over the external surface of fixed inner tube 654*b*, thereby sealing its distal opening while allowing it to be easily moved distally or proximally thereon by the operator.

Sealant 64*c* may be applied to the proximal end of fixed inner tube 654*b* in order to provide enhanced sealing of the distal opening of inner tube 654*a*. Sealing of the distal opening of fixed inner tube 654*b* may be achieved by an annular gasket 64 attached to the proximal tip of external slidable tube 613*a* such that a proximal portion thereof is pressed against an annular portion of the outer surface of fixed inner tube 654*b*.

Gaskets 64 can be made of a flexible material such as silicone or polyurethane. Alternatively, gaskets 64 may be implemented by an added lubricant such as mineral oil or silicone oil which improves the sliding between the tubes. The sealing may be further increased by increasing the pressure in the balloon.

It should be noted that tubes 613*a* and 654*a* may be fixed tubes such that tube 654*a* is fixed to the shaft 663 and tube 613*a* is fixed to the distal neck of balloon 611*a*, such that tube 654*b* can slide into both tubes.

The structure, geometrical dimensions of elements of catheter 650 designated by the same numerals, and the method of manipulating of its length and balloon's volume and shape, are much the same to those elements and manipulating method which were previously described hereinabove and therefore will not be discussed here, for the sake of brevity. Fixed inner tube 654*a* and external slidable tube 613*a* may be manufactured by an extrusion and laser cutting process from a plastomeric or metallic type of material, preferably from nylon or flexible metal. Their diameters are adapted to provide tight fitting and the necessary sealing of distal openings of inner tube 654*a* and of fixed inner tube 654*b*.

Figure 14A:
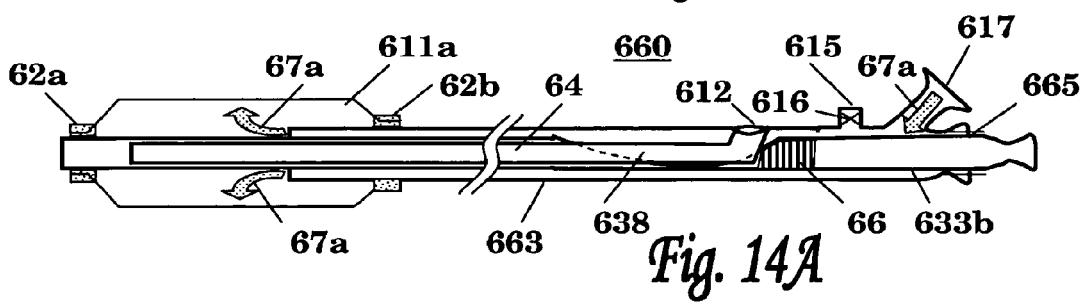
FIGS. 14A to 14C show longitudinal section views of a rapid exchange catheter according to a sixth preferred embodiment of the invention wherein the inner tube of the catheter is encompassed in a slidable intermediate tube.
Figure 14B:
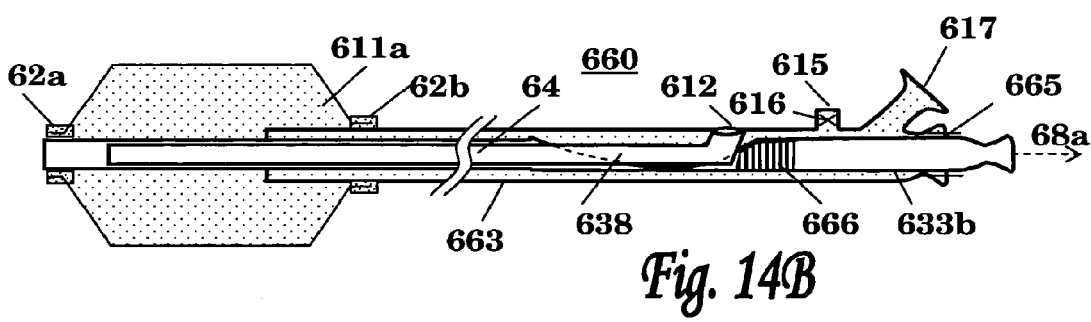
Figure 14C:
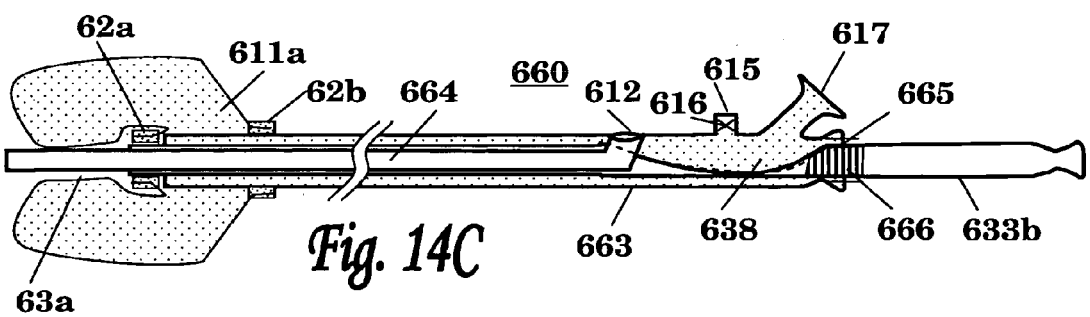

FIGS. 14A to 14C show longitudinal section views of a sixth preferred embodiment of the invention in which the inner tube 64 of catheter 660 is encompassed in a slidable intermediate tube 633*b*. In this preferred embodiment the distal end of balloon 611*a* is attached to the slidable intermediate tube 633*b* at distal attachment points 62*a* provided around the outer surface of a distal section of said slidable intermediate tube. Horizontal opening 638 is provided on an upper side of slidable intermediate tube 633*b*. Tube 64 protrudes upwardly through horizontal opening 638 towards the upper side of hollow shaft 66 at the location in which it is affixed thereto and provide an access to its lumen via lateral port 612.

During a procedure balloon 611*a* may be inflated by pressurized fluid (designated by arrows 67*a* in FIG. 14A) provided via inflation fluid port 617. As illustrated in FIG. 14B, pressurized fluid passes through the hollow interior of hollow shaft 663 into the internal space of balloon 611*a*. The catheter and its balloon in the inflated state are illustrated in FIG. 14B. The proximal section of intermediate tube 633*b* between horizontal opening 638 and the proximal end of intermediate tube 633*b* may be sealed by a sealant 666 in order to prevent entry of inflation fluids thereinto. Whenever the pressure in balloon 611*a* and hollow interior of hollow shaft 663 is greater than a predetermined threshold value, a portion of inflation fluids are discharged via discharge valve 616 installed in discharge valve outlet 615.

The proximal section of intermediate tube 633*b* protrudes proximally via proximal opening 665 provided at the proximal end of shaft 663. Proximal opening 665 is designed to conveniently allow the sliding of intermediate tube 633*b* therethrough while providing suitable sealing thereof and preventing leakage of inflation fluid therefrom. Manipulation of the catheter's length and its balloon's shape and volume are performed by sliding the intermediate tube 633*b* proximally or distally relative to the catheter's shaft.

For example, after inflating balloon 611*a* the operator may pull the proximal section of intermediate tube 633*b* (designated by arrow 68*a* in FIG. 14B) thereby causing distal section of balloon 611*a* to collapse and fold inwardly and deform cavity 63*a*, as illustrated in FIG. 14C. Horizontal opening 638 is adjusted to allow sliding intermediate tube 633*b* proximally into a state in which attachment point 62*a* reaches proximal end of shaft 663, and on the other hand, to allow sliding intermediate tube 633*b* sufficiently distally and enable stretching the full length of balloon 611*a*.

Intermediate tube 633*b* may be manufactured by extrusion or laser cutting processes, from a plastomer or metallic type of material such as nylon, Teflon, or flexible stainless steel. The diameters of inner tube 664 and of intermediate tube 633*b* are adapted to allow insertion of inner tube into the lumen of intermediate tube 633*b* while providing suitable sealing thereof and preventing leakage of inflation fluids thereinto. For example intermediate tube 633*b* may have an inner diameter of about 0.8 mm and the outer diameter of inner tube 664 may be of about 0.78 mm.

Intermediate tube 633*b* can be manufactured by an extrusion process in which the ID (internal diameter) has an appropriate tolerance to fit over the outer diameter of inner tube 664. Inner tube 664 and intermediate tube 633*b* are assembled together such that lateral port 612 is located in the horizontal opening 638 of intermediate tube 633*b*. Thereafter the tubes 664 and 633*b* are inserted into the hollow shaft 663 and lateral port 612 can be attached to hollow shaft 663.

It should be noted that intermediate tube 633*b* is not necessarily a complete tube. While the distal portion of intermediate tube 633*b* should be of a tubular shape, its proximal portion may have other cross-sectional shapes such as a semilunar shape. Alternatively, proximal portion of intermediate tube 633*b* may be implemented by a wire attached to its distal portion and exiting catheter 660 via proximal opening 665.

FIGS. 15A to 15C show longitudinal section views of a catheter 670 according to a seventh preferred embodiment of the invention wherein the inner tube 674 is made movable by affixing it to a slidable sealing sleeve 679. In this preferred embodiment the distal end of balloon 611*a* is attached to the inner tube 674 at distal attachment points 62*a* provided around the outer surface of a distal section of said inner tube.

The structure, geometrical dimensions of elements of catheter 670 designated by the same numerals, and the method of manipulating its length and balloon's volume and shape, are much the same as those elements and manipulating method which were previously described hereinabove and therefore will not be further discussed herein, for the sake of brevity.

As with previous embodiments of the invention the inner tube is disposed in the hollow interior of the catheter's hollow outer shaft 676 and a curved section 637 thereof comprising lateral port 612 protrudes outwardly therefrom. A lateral opening 69 is provided on hollow outer shaft 676 from which said curved section 637 of inner tube 674 is protruding outwardly from hollow shaft 676. Lateral opening 69 is sealed by sealing sleeve 679 mounted over an outer surface of hollow outer shaft 676. Sealing sleeve 679 is designed to tightly fit over the outer surface of hollow outer shaft 676, and to seal lateral opening 69 and the attachment area between sealing sleeve 679 and the curved section 637 of inner tube 674 protruding therefrom. Moreover, sealing sleeve is also made slidable to allow its movement distally or proximally within the limits imposed by lateral opening 69.

In this way a movable inner tube 674 is obtained. The operator may inflate (designated by arrows 67*a* in FIG. 15A) balloon 611*a* and move inner tube distally or proximally by sliding sealing sleeve 679 over hollow shaft 676. Additionally or alternatively, a displacement rod 648 may be employed for this purpose. Displacement rod 648 may be attached to a proximal section of inner tube 674 and a proximal section thereof can be made available to the operator via a proximal opening 675 provided at the proximal end of hollow shaft 676. Proximal opening 675 is designed to allow conveniently sliding displacement rod 648 therethrough while providing suitable sealing thereof and preventing leakage of inflation fluid therefrom.

Lateral opening 69 is adjusted to allow moving inner tube 674 proximally into a state in which attachment point 62*a* reaches the proximal end of hollow shaft 676, and on the other hand, to allow moving inner tube 674 sufficiently distally and enable stretching balloon 611*a* to its fullest length.

Sealing sleeve 679 can be manufactured by an extrusion and laser cutting process from a plastomer or metallic type of material, preferably from nylon or flexible stainless steel. The sealing and attachment of sealing sleeve 679 and the curved section 637 of inner tube 674 is preferably obtained by bonding these parts together by thermo-bonding or any other adhesive method such that they can slide together. The diameter of sealing sleeve 679 is adjusted according to the geometrical dimensions of hollow shaft 676. For example, if the diameter of hollow shaft is about OD (outer diameter) 1.2 mm then the diameter of sealing sleeve is made about ID 1.22 mm.

FIG. 15C demonstrates an implementation of catheter 670*a*, similar to catheter 670, wherein an inner sealing sleeve 677 is adapted to be installed in the hollow interior of hollow shaft 676. In this implementation inner sealing sleeve 677 is adapted to be pressed against the inner wall of hollow shaft 676 about the area of lateral opening 69 and thereby to provide suitable sealing thereof. As in catheter 670 illustrated in FIG. 15A, vertical section of inner tube 674 protrudes outwardly via inner sealing sleeve 677 and may be accessed by the operator via lateral port 612. The sealing and attachment of inner sealing sleeve 677 and vertical section of inner tube 674 may be obtained using the same means described above with reference to catheter 670.

Inner sealing sleeve 677 can be manufactured by an extrusion and laser cutting process from a plastomeric or metallic type of material, preferably from nylon or flexible stainless steel. The sealing and attachment of inner sealing sleeve 677 and the vertical section of inner tube 674 is preferably obtained in a similar manner as was explained hereinabove. The diameter of sealing sleeve 677 is adjusted according to the geometrical dimensions of hollow shaft 676. For example, if the diameter of hollow shaft is about ID 1 mm then the diameter of inner sealing sleeve is made about OD 0.98 mm.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different tubes, balloons, shafts, and other members, described hereinabove may be constructed in different shapes (e.g. having oval, square etc. form in plan view) and sizes from those exemplified in the preceding description.

It should be noted that the different balloon catheter embodiments of the invention which were described hereinabove may be implemented with different types of balloon enabling folding of the proximal section of the balloon, the distal section of the balloon, or both proximal and distal sections of the balloon, as was exemplified hereinabove with reference to FIGS. 9D and 9E.

In particularly preferred embodiments of the RE catheter system of the present invention, the balloon shape and force resistance characteristics of the catheter tubing are as described hereinabove in connection with the OTW systems, and exemplified in the following two Examples.

EXAMPLES

Example 1

Finite Element Analysis (FEA) of a Debris-Collecting Balloon for Use in the Present Invention FEA is a computerized tool which was used to optimize the balloon design in order to improve its ability to fold in the desired way. The FE model describes an inflated balloon which its edge is retracted, resulting in folding of the balloon. The simulation was performed on different balloon designs and at varied inflation pressures, taking into account the mechanical properties of the balloon material, which was chosen to be nylon 12 or pebax.

Assumptions:

i. The balloon is made of a homogenous and isotropic material.

ii. The balloon's shape is symmetrical around its longitudinal axis.

iii. The balloon's shape is symmetrical around its mid transverse axis.

iv. The folding results in flexural stresses in the balloon material. Thus the mechanical properties (Modulus and Poisson Ratio) of the substance when flexed are taken into account in the FE analyses.

Figure 6:
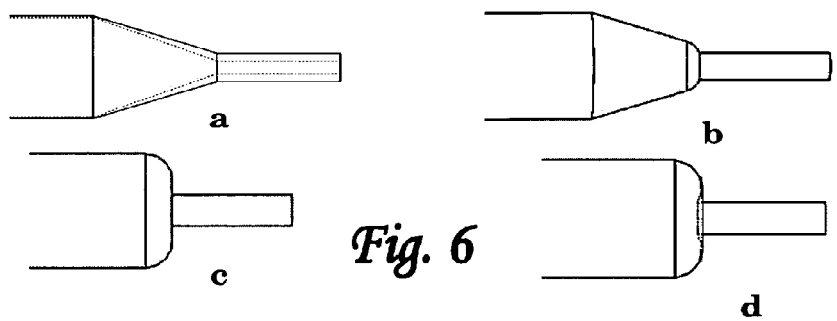
FIG. 6 schematically illustrates the four balloon designs that were analyzed and compared in the finite element analysis study: a. Standard 20° tapering; b. 20° tapering with smooth round ending; c. Round ending; d. Round ending with initial retracting.

Methods:

a) The analyses were performed using a nonlinear Finite Elements Analysis (FEA) program MSC.MARC. This software allows assessment of the structural integrity and performance of parts undergoing large deformations as a result of thermal or structural load (www.mscsoftware.com).

b) The analyses were nonlinear, assuming large displacements and taking into account stiffness change due to geometry update and sequential forces.

c) The model was 2D axisymmetric.

d) The model consisted of about 1000 nodes and 1000 2D solid elements.

e) Constant pressure was applied from within the balloon on its walls, reflecting the inflation pressure. Simultaneously, gradually increased axial force was exerted to the edge of the balloon, results in its folding. The displacement of the balloon wall in the horizontal (longitudinal) axis was measured versus the applied force.

f) The longitudinal axis of the balloon was kept fixed, while the balloon walls were free to move/fold as a result of the axial load.

g) The balloon's specifications are listed in the following table:

| Balloon Specifications | |
|---|---|
| Balloon length [mm] | 20 |
| Balloon Outer Diameter [mm] | 3 |
| Tube Outer Diameter [mm] | 0.4 |
| Balloon Body Wall Thickness [μm] | 10 |
| Neck Wall Thickness [μm] | 50 |
| Tube Wall Thickness [μm] | 100 |
| Tapering | varying |
| Material | PET (Polyethylene Terephthalate) |
| Mechanical Properties | |
| Flexural Modulus [Kg/mm$^2$] | 100 |
| Flexural Yield Strength [Kg/mm$^2$] | 8.15 |
| Poisson Ratio | 0.4 | h) Four balloon designs were analyzed, wherein the differences reside in the design of their tapering (see FIG. 6):

Standard 20° tapering

20° tapering with smooth round ending

Round ending

Round ending with initial retracting i) The simulations were performed at five different inflation pressures: 1, 3, 6, 9 and 12 atmospheres.

Figure 7:
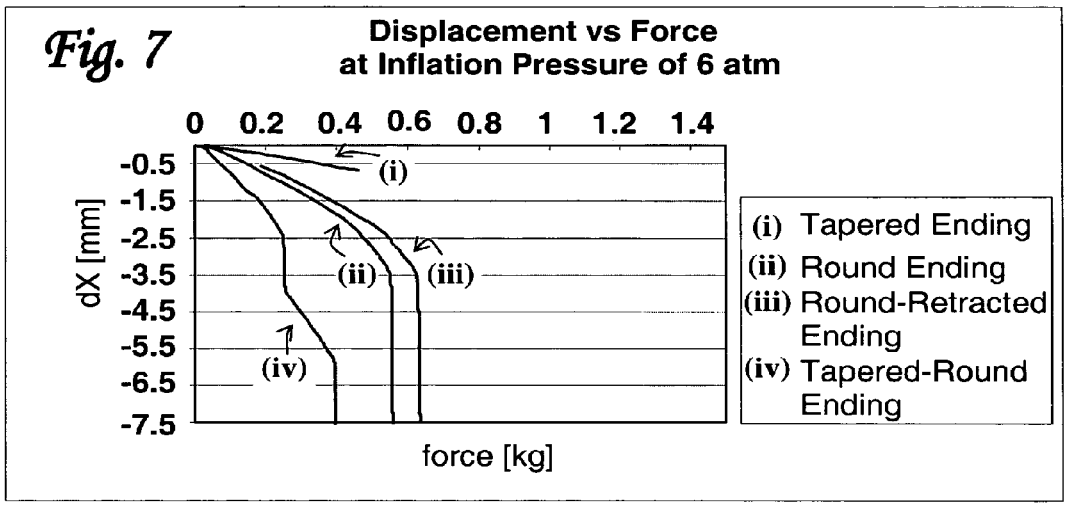
FIG. 7 graphically depicts the displacement vs. retracting force for the four balloon shapes, compared at an inflation pressure of 6 atmospheres.

Results:

FIG. 7 shows the displacement vs. retracting force for the four balloon shapes at an inflation pressure of 6 atmospheres. Considering the maximal force required for collapse of the balloon, the Tapered-Round Ending Balloon required the lowest force, whereas the Round Ending Balloons need the greatest force to collapse. The Tapered Ending Balloon is somewhere between them. The slope of the Tapered Ending Balloon in the initial phase seems to be relatively moderate compared to the other balloon configurations. The moderate slope indicates higher stiffness. In other words, higher force is required to induce a given displacement. The slope of the Tapered-Round Ending Balloon is the steepest one, and suggests relatively high compliance to folding.

The balloon retracted shape vs. the original shape, at different inflation pressures was also studied (results not shown). The results demonstrated that the Tapered Ending Balloon is barely retracted, compared to the Round Ending Balloons which are retracted in a more smooth and continuous fashion. This is in spite of the higher force required to fold them.

Conclusion:

From the above analyses it was concluded that the inflation pressure and the balloon geometry have an important role in determining of the required folding force and the folding style. It appears that a tapered balloon with a smooth round ending folds best and has a relatively low retracting force, when compared to standard tapered balloon or a balloon with a round ending.

Example 2

Determination of the Force that is Required in Order to Fold the Balloon at Different Inflation Pressure Equipment and Materials:

3.0 mm Nylon 12 Vestamid L2101F Balloon (Interface Associates 316079-1)

Glass tube with inner diameter of 3 mm.

Guidant HI-TORQUE CROSS-IT 200XT 0.014" Guidewire.

Hounsfield Test Equipment Model TX0927, 50-N load cell. This computer controlled testing machine enables determining tension, compression, shear, flexure and other mechanical and physical properties of materials. The machine provides selection of test speeds and direction of travel. It can measure the force and displacement values and can also graphically display the test.

Assouline Compressor type 1.5 HP.

Fluid dispensing system Model 1500XL.

Procedure:

The balloon was inserted into a 3-mm glass tube, at straight position or inclined to 45°. A guidewire was inserted into the inner tube in order to stabilize the folding motion. The balloon was inflated using a compressor and the inflation pressure was controlled by a dispenser. The procedure was performed at pressures ranging between 3-7 atm, with increments of 1 atm. The balloon was folded using the Hounsfield Test machine, by pulling the inner tube at speed of 100 mm/min up to 20 mm, and then pushing back at the same speed until the balloon was completely unfolded.

Four tests were conducted at each pressure, to confirm that the results could be replicated.

Figure 8:
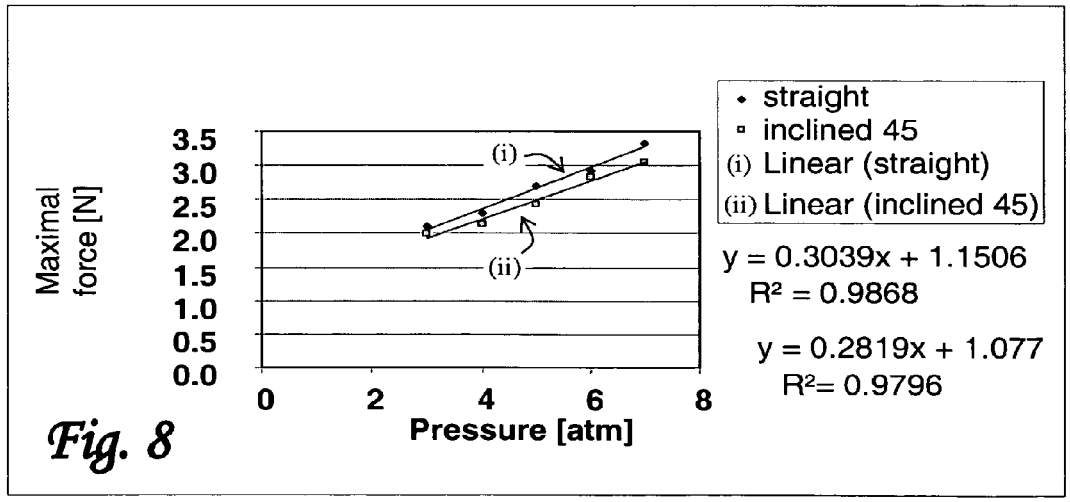
FIG. 8 graphically depicts the maximum force generated in the catheter tubes following balloon folding, measured for different balloon inflation pressures.

Results:

The maximal force required for folding the balloon at each pressure is presented in FIG. 8 The maximal force increases with the inflation pressure for both positions (straight and inclined) and ranges between 2-3.5 N (200-350 gr) with increments vary between 0.2-0.4 N (20-40 gr) per step of 1 atm in pressure. Higher inflation pressure requires greater force to fold the balloon. The relationship is approximately linear ($R^2$=0.98). The maximal forces are slightly lower for the inclined position; however, repeated tests at the straight position revealed that the lesser forces result from the material fatigue. To support this assumption, visual examination of the balloon after 40 repeats showed that the balloon material lost its flexibility and looked crumpled.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A balloon catheter comprising:
    an outer conduit having an outer surface;
    an inner conduit having an outer surface, the inner conduit is suitable for passage over a guide wire, the inner conduit is movably disposed within a lumen of the outer conduit, wherein a distal tip of the inner conduit extends beyond a distal tip of the outer conduit at all times during operation of the catheter, and
    wherein the inner conduit is capable of being moved along its longitudinal axis in relation to the outer conduit;

a balloon having a lumen, a proximal margin, and a distal margin, wherein the proximal margin of the balloon is attached to an outer surface of the distal tip of the outer conduit and the distal margin of the balloon is attached to an outer surface of the portion of the inner conduit that extends beyond the distal tip of the outer conduit, and wherein the distal and/or proximal end portion(s) of the balloon are capable of intussuscepting upon proximal movement of the inner conduit in relation to the outer conduit to form a cavity within the balloon, such that, after said intussuscepting, when the balloon is deflated, the cavity is enlarged trapping therewithin debris and/or particulate matter without need for application of externally applied suction; and a fluid port for introducing an expansion fluid into an annular space formed between the inner surface of the outer conduit and the outer surface of the inner conduit and therefrom into the lumen of the balloon, and for the removal of the expansion fluid.

2. The balloon catheter according to claim 1, wherein the distal portion of the balloon is capable of intussuscepting upon proximal movement of the inner tube in relation to the outer tube.

3. The balloon catheter according to claim 1, wherein the inner and outer conduits are characterized by their ability to withstand axially directed forces in the range of between 2 and 20 Newton without undergoing significant deformation.

4. The balloon catheter according to claim 3, wherein the inner and/or outer conduits are constructed from a material selected from the group consisting of a biocompatible polymer, nylon, a braided nylon thread, a nylon thread that has undergone orientation treatment, flexible stainless steel tubing, a polymer tube with metal mesh reinforcement, reinforced Pebax®, polyurethane and PET.

5. The balloon catheter according to claim 1, wherein the balloon is characterized by having, in its inflated state, a shape which is capable of guiding the intussuscepting of the distal and/or proximal portion(s) thereof upon proximal movement of the inner conduit in relation to the outer conduit.

6. The balloon catheter according to claim 5, wherein the balloon is characterized by having, in its inflated state, a distal taper with a rounded distal extremity.

7. The balloon catheter according to claim 5, wherein the balloon is characterized by having, in its inflated state, a proximal taper with a rounded proximal extremity.

8. The balloon catheter according to claim 1, also including an automatic pressure regulating mechanism for automatically resolving overpressure conditions within the annular space and the balloon upon the proximal movement of the inner conduit in relation to the outer conduit.

9. The balloon catheter according to claim 8, wherein the automatic pressure regulating mechanism is selected from, an overpressure valve in fluidic communication with the annular space;

a syringe-like structure, having a barrel portion and a plunger, positioned at the proximal end of the catheter system, wherein the barrel portion of the syringe-like structure is formed by an expanded portion of the outer conduit, and wherein the plunger of the syringe-like structure co-axially surrounds the proximal end of the inner conduit, and is affixed thereto, an inflatable member attached to the opening of an outlet formed in the outer conduit, the outer tube, or portions thereof, being inflatable such that over-pressure conditions may be resolved by its expansion, and any combinations thereof.

10. The balloon catheter system according to claim 8, wherein the automatic pressure regulating mechanism comprises an overpressure valve for discharging inflation fluid whenever overpressure conditions develop in the lumen of the outer conduit.

11. The balloon catheter system according to claim 8, wherein the automatic pressure regulating mechanism comprises an overpressure valve for discharging inflation fluid whenever the pressure in the balloon and the inner lumen of the outer conduit reaches a set point.

12. The balloon catheter system according to claim 8, wherein the set point is in the range of 1-25 atmospheres.

13. The balloon catheter system according to claim 8, wherein the automatic regulating mechanism comprises a syringe-like structure, having a barrel portion and a plunger, positioned at the proximal end of the catheter system, wherein the barrel portion of the syringe-like structure is formed by an expanded portion of the outer conduit, and wherein the plunger of the syringe-like structure co-axially surrounds the proximal end of the inner conduit, and is affixed thereto, wherein when the inner conduit is proximally pulled the plunger moves proximally within the barrel portion to automatically accommodate excess inflation fluid ejected from the balloon during the intussuscepting of the balloon, to prevent overpressure conditions from developing within the balloon.

14. The balloon catheter system according to claim 1, wherein the catheter also includes a graduated scale formed on the inner conduit for determining the length of the inner conduit that has been proximally retracted from the outer conduit.

15. The balloon catheter system according to claim 1, wherein the catheter also includes a locking mechanism for locking the inner conduit to prevent it's axial movement within the outer conduit and for releasing the inner conduit to enable its axial movements within the outer conduit.

16. The balloon catheter system according to claim 15, wherein the locking mechanism comprises a safety lock sealingly and movably disposed within a tight orifice formed in the proximal end of the outer conduit and attached U-shaped gripping clip attached to the safety lock and movably disposed within the outer conduit, the gripping clip is adapted for gripping the outer surface of the inner conduit when the safety lock is pushed radially inwardly towards the inner conduit to prevent proximal and distal movement of the inner conduit relative to the outer conduit and to release the inner conduit when the safety lock is pulled radially outwardly away from the inner conduit to enable proximal and distal movement of the inner conduit relative to the outer conduit.

17. The balloon catheter system according to claim 1, wherein the catheter is adapted to operate within a predetermined pressure range of 1-25 atmospheres.

18. The balloon catheter system according to claim 1, wherein the inner conduit, the balloon and the outer conduit have a shape selected from the group consisting of a tubular shape, an oval shape and a square shape.

19. A method for collecting debris from an internal passage of a mammalian subject, the method comprises the steps of:

a) inserting a balloon catheter as defined in claim 1 into the internal passage, and advancing the catheter until the distal tip thereof has reached a site, at which it is desired to collect debris;
b) inflating the balloon with expansion fluid;
c) pulling the inner conduit of the catheter in a proximal direction, causing the intussuscepting of the distal and/or proximal end portion(s) of the balloon;
d) deflating the balloon, to form a cavity into which debris and/or particulate matter is collected and entrapped without the need of applying of suction from an external source; and
e) removing the balloon catheter from the internal passage of the subject, together with the entrapped debris and/or particulate matter.

20. The method according to claim 19, wherein the internal passage is a blood vessel.

* * * * *